(12) United States Patent
Mou et al.

(10) Patent No.: US 12,137,756 B2
(45) Date of Patent: Nov. 12, 2024

(54) SMART CLOTH

(71) Applicant: MICROJET TECHNOLOGY CO., LTD., Hsinchu (TW)

(72) Inventors: Hao-Jan Mou, Hsinchu (TW); Ching-Sung Lin, Hsinchu (TW); Chih-Kai Chen, Hsinchu (TW); Chi-Feng Huang, Hsinchu (TW); Yung-Lung Han, Hsinchu (TW); Chin-Wen Hsieh, Hsinchu (TW)

(73) Assignee: MICROJET TECHNOLOGY CO., LTD., Hsinchu (TW)

( * ) Notice: Subject to any disclaimer, the term of this patent is extended or adjusted under 35 U.S.C. 154(b) by 863 days.

(21) Appl. No.: 17/307,233

(22) Filed: May 4, 2021

(65) Prior Publication Data
US 2021/0345691 A1 Nov. 11, 2021

(30) Foreign Application Priority Data
May 8, 2020 (TW) .................... 109115433

(51) Int. Cl.
*A41D 1/00* (2018.01)
*A41D 13/002* (2006.01)
(Continued)

(52) U.S. Cl.
CPC ............. *A41D 1/005* (2013.01); *A41D 27/28* (2013.01); *A61B 5/02055* (2013.01);
(Continued)

(58) Field of Classification Search
CPC .......... A61F 2007/00093; A41D 27/28; A41D 27/285; A41D 13/1281; A41D 13/0025
See application file for complete search history.

(56) References Cited

U.S. PATENT DOCUMENTS 10,952,623 B2 * 3/2021 Mou .................. A61B 5/02141
11,737,676 B2 * 8/2023 Mou .................. A61B 5/02141
600/493
(Continued)

FOREIGN PATENT DOCUMENTS

CN 1270793 A 10/2000
CN 107260148 A 10/2017
(Continued)

*Primary Examiner* — Kaitlyn E Smith
(74) *Attorney, Agent, or Firm* — Birch, Stewart, Kolasch & Birch, LLP

(57) ABSTRACT

A smart cloth includes a cloth body, a control body, actuation air-permeable components, temperature sensing components, and a health-monitoring device. The health-monitoring device includes a bio-sensing module, a blood glucose sensor, a blood pressure measurement module, and a gas bag. The temperature information of the wearer is detected by the temperature sensing components and outputted to the microprocessor of the control body, so that the microprocessor controls the actuation air-permeable components to perform the gas-guiding operation to adjust an apparent temperature of the wearer for providing wearing comfortableness. The bio-sensing module, the blood glucose sensing module, and the blood pressure measurement module detect and provide the detection data information for the wearer anytime and in real-time to provide health-related information to the wearer. Furthermore, the smart cloth may include a gas detection module, allowing the wearer to obtain gas data information anytime and anywhere for alerting and notifying the wearer.

20 Claims, 25 Drawing Sheets

(51) Int. Cl.

| | |
|---|---|
| *A41D 27/28* | (2006.01) |
| *A61B 5/00* | (2006.01) |
| *A61B 5/0205* | (2006.01) |
| *A61B 5/022* | (2006.01) |
| *A61B 5/145* | (2006.01) |
| *A61B 5/1455* | (2006.01) |
| *A61B 5/332* | (2021.01) |
| *A61F 7/00* | (2006.01) |
| *G01N 15/06* | (2024.01) |
| *G01N 15/075* | (2024.01) |
| *G01N 15/14* | (2024.01) |
| *G01N 33/00* | (2006.01) |
| *G16H 20/30* | (2018.01) |
| *G16H 40/67* | (2018.01) |
| *G16H 50/20* | (2018.01) |

(52) U.S. Cl.
CPC ........ *A61B 5/02233* (2013.01); *A61B 5/4836* (2013.01); *A61B 5/6804* (2013.01); *A61F 7/00* (2013.01); *G01N 15/06* (2013.01); *G01N 15/14* (2013.01); *G01N 33/0047* (2013.01); *G16H 20/30* (2018.01); *G16H 40/67* (2018.01); *G16H 50/20* (2018.01); *A41D 13/0025* (2013.01); *A61B 5/14532* (2013.01); *A61B 5/14552* (2013.01); *A61B 5/332* (2021.01); *A61F 2007/006* (2013.01); *A61F 2007/0093* (2013.01); *G01N 15/075* (2024.01); *G01N 2015/1493* (2013.01)

(56) References Cited

U.S. PATENT DOCUMENTS

| | | | |
|---|---|---|---|
| 11,744,474 B2* | 9/2023 | Mou | .................... A61B 5/0235 600/498 |
| 11,937,903 B2* | 3/2024 | Mou | .................... A61B 5/0235 |
| 11,944,412 B2* | 4/2024 | Mou | ................. A61B 5/02141 |
| 2019/0150806 A1* | 5/2019 | Mou | ................. A61B 5/150984 |
| 2020/0129122 A1* | 4/2020 | Mou | .................. A61B 5/02233 |
| 2020/0229320 A1* | 7/2020 | Mou | .................... A41D 13/002 |

FOREIGN PATENT DOCUMENTS

| | | |
|---|---|---|
| CN | 209055518 U | 7/2019 |
| CN | 110179449 A | 8/2019 |
| CN | 110447988 A | 11/2019 |
| CN | 209959441 U | 1/2020 |
| CN | 110873682 A | 3/2020 |
| CN | 210130826 U | 3/2020 |
| TW | M580133 U | 7/2019 |
| TW | M581637 U | 8/2019 |
| TW | 202014117 A | 4/2020 |
| TW | 202014979 A | 4/2020 |

\* cited by examiner

SMART CLOTH

CROSS-REFERENCE TO RELATED APPLICATION

This non-provisional application claims priority under 35 U.S.C. § 119(a) to Patent Application No. 109115433 filed in Taiwan, R.O.C. on May 8, 2020, the entire contents of which are hereby incorporated by reference.

BACKGROUND

Technical Field

The present disclosure relates to a smart cloth, in particular, to a smart cloth where the cloth body of the smart cloth is equipped with a health-monitoring device that is capable of adjusting the apparent temperature of the wearer.

Related Art

Clothes are necessities in daily lives. The wearing comfortableness of cloth is an issue need to be concerned wherein the wearing comfortableness of cloth should consider the air permeability in accordance with the apparent temperature of the wearer changes. Therefore, the air permeability of the cloth is an important issue need to be taken into consideration for developing smart clothes. Furthermore, due to the increasing life pace and workload, more and more people start work out. Consequently, apparatuses that can track the wearers' health become popular. These apparatuses can record health data and allow the wearer to track the progress during work out. Therefore, how to provide a cloth device that can monitor the health record of the wearer is also an important issue for being developed. Moreover, nowadays people pay more and more attention to monitoring ambient air quality in daily life, such as carbon monoxide, carbon dioxide, volatile organic compounds (VOC), PM2.5, nitric oxide, and sulfur monoxide etc., and the particle suspended in the air, which can cause adverse health effects on the human body when exposure to these gases, and can even be life-threatening. Hence, the quality of the ambient air should be paid more attention thereto. Therefore, how to monitor the quality of the ambient air so as to prevent exposing or to apply precautions to hazardous gases is also an important issue to be paid attention to.

SUMMARY

One object of the present disclosure is to provide a smart cloth, the smart cloth is able to detect the temperature information of the wearer through the temperature sensing components and outputs the temperature information of the wearer to the microprocessor of the control body, so that the microprocessor is able to control the actuation pumps of the actuation air-permeable components to perform the gas-guiding operation so as to adjust the apparent temperature of the wearer and provide wearing comfortableness. Moreover, the bio-sensing module, the blood glucose sensing module, and the blood pressure measurement module of the health-monitoring device can detect and provide the detection data information to the wearer anytime and in real-time so as to provide the health-related information to the wearer. Furthermore, the gas detection module can detect the gas to obtain the gas data information anytime and anywhere. Therefore, the smart cloth can alert or notify the person who is exposed to the hazardous gas, so that the person can leave the place immediately or take precautions for the hazardous gas. Hence, the smart cloth of this invention can prevent the wearer from having adverse impact in health or resulting in damages due to the exposure of hazardous gases. Accordingly, the smart cloth can have benefits of adjusting the apparent temperature of the wearer to provide wearing comfortableness, detecting the health record anytime and anywhere, and monitoring the air quality of ambient air.

A general embodiment of the present disclosure provides a smart cloth including a cloth body, a control body, a plurality of actuation air-permeable components, a plurality of temperature sensing components, and a health-monitoring device. The cloth body comprises a pair of sleeves. The control body comprises a microprocessor and a driving battery, and the microprocessor is connected to the driving battery. The microprocessor is capable of generating a first driving signal and a second driving signal, receiving temperature information and a plurality of detection data information, and outputting the first driving signal, the second driving signal, and the plurality of detection data information. The actuation air-permeable components are woven with and positioned on the cloth body. The actuation air-permeable components comprise a plurality of actuation pumps. The actuation pumps are series-connected to the microprocessor of the control body through conductors to receive the first driving signal of the microprocessor to perform a gas-guiding operation. The temperature sensing components are woven with and positioned on the cloth body. The temperature sensing components comprise a plurality of temperature sensors. The temperature sensors are series-connected to the microprocessor of the control body through conductors. The temperature sensors are capable of attaching to skin of a wearer to detect and generate the temperature information and output to the microprocessor, so that the microprocessor receives and calculates the temperature information so as to generate and provide the first driving signal to the actuation pumps for performing the gas-guiding operation. The health-monitoring device is woven with and positioned on the cloth body. The health-monitoring device includes a bio-sensing module, a blood glucose sensor, a blood pressure measurement module, and a gas bag, wherein the bio-sensing module, the blood glucose sensor, and the blood pressure measurement module are connected to the microprocessor of the control body through conductors. The gas bag is woven with and positioned on one of the pair of the sleeves of the cloth body. The blood pressure measurement module is connected to the gas bag. The bio-sensing module and the blood glucose sensor are capable of attaching to the skin of the wearer to generate the plurality of detection data information and provide the plurality of detection data information to the microprocessor for output. The blood pressure measurement module receives the second driving signal of the microprocessor to perform the gas-guiding operation so as to inflate the gas bag worn on an arm portion of the wearer, such that the blood pressure measurement module is capable of detecting a blood pressure of the wearer to generate the plurality of detection data information and providing the plurality of detection data information to the microprocessor for output. The temperature information of the wearer is detected by the temperature sensing components and outputted to the microprocessor of the control body, so that the microprocessor is able to control the actuation pumps of the actuation air-permeable components to perform the gas-guiding operation so as to adjust an apparent temperature of the wearer and provide wearing comfortableness. The bio-sensing module, the blood glucose sensing module, and the blood pressure measurement module of the health-monitoring device is able to detect the plurality of detection data information. Moreover, the bio-sensing module, the blood glucose sensing module provide the plurality of detection data information to the wearer anytime and in real-time so as to provide the health-related information to the wearer.

BRIEF DESCRIPTION OF THE DRAWINGS

The disclosure will become more fully understood from the detailed description given herein below, for illustration only and thus not limitative of the disclosure, wherein.

DETAILED DESCRIPTION

The present disclosure will now be described more specifically with reference to the following embodiments. It is to be noted that the following descriptions of different embodiments of this disclosure are presented herein for purpose of illustration and description only, and it is not intended to limit the scope of the present disclosure.

Figure 1:
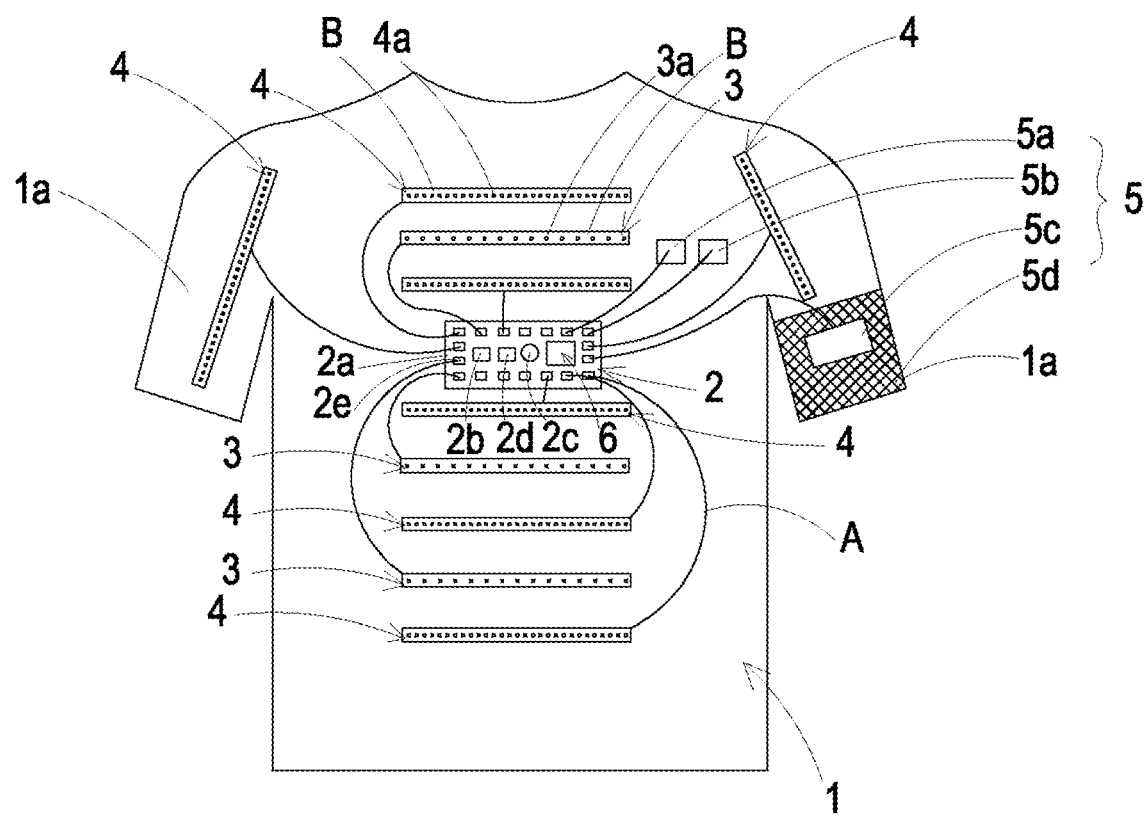
FIG. 1 illustrates a schematic view of a smart cloth according to an exemplary embodiment of the present disclosure.
Figure 2:
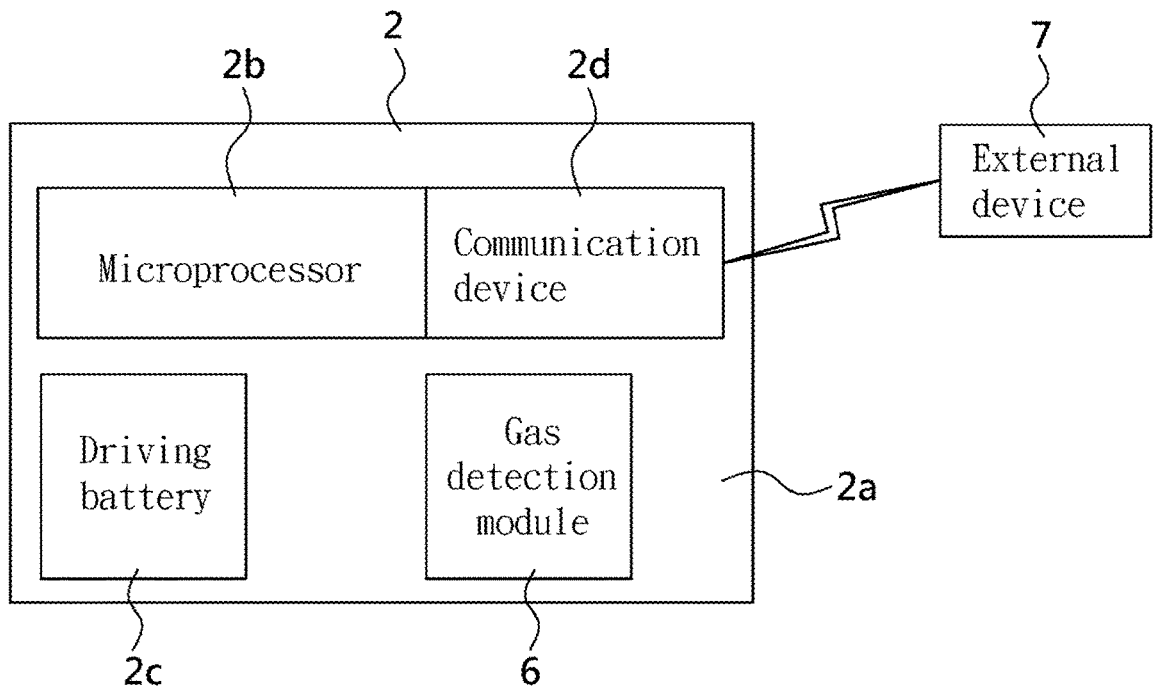
FIG. 2 illustrates a schematic view showing that an external device is connected to the control body of the smart cloth according to an exemplary embodiment of the present disclosure.

Please refer to FIG. 1 and FIG. 2. A smart cloth including a cloth body 1, a control body 2, a plurality of temperature sensing components 3, a plurality of actuation air-permeable components 4, and a health-monitoring device 5 is provided. The cloth body 1 includes a pair of sleeves 1a. The control body 2 includes a control main board 2a, a microprocessor 2b, a driving battery 2c, a communication device 2d, and a plurality of contacts 2e. The microprocessor 2b, the driving battery 2c, and the communication device 2d are packaged with and disposed on the control main board 2a. The microprocessor 2b is connected to the driving battery 2c and is capable of generating a first driving signal and a second driving signal, receiving temperature information and a plurality of detection data information, and outputting the first driving signal, the second driving signal, and the detection data information. The detection data information received by the microprocessor 2b is transmitted to an external device 7 through the communication device 2d for being stored, processed, and applied by the external device 7. The contacts 2e are provided for connecting the temperature sensing components 3, the actuation air-permeable components 4, and the health-monitoring device 5 to the microprocessor 2b through conductors A. The external device 7 may be one of a cloud system, a portable device, and a computer system.

Figure 3A:
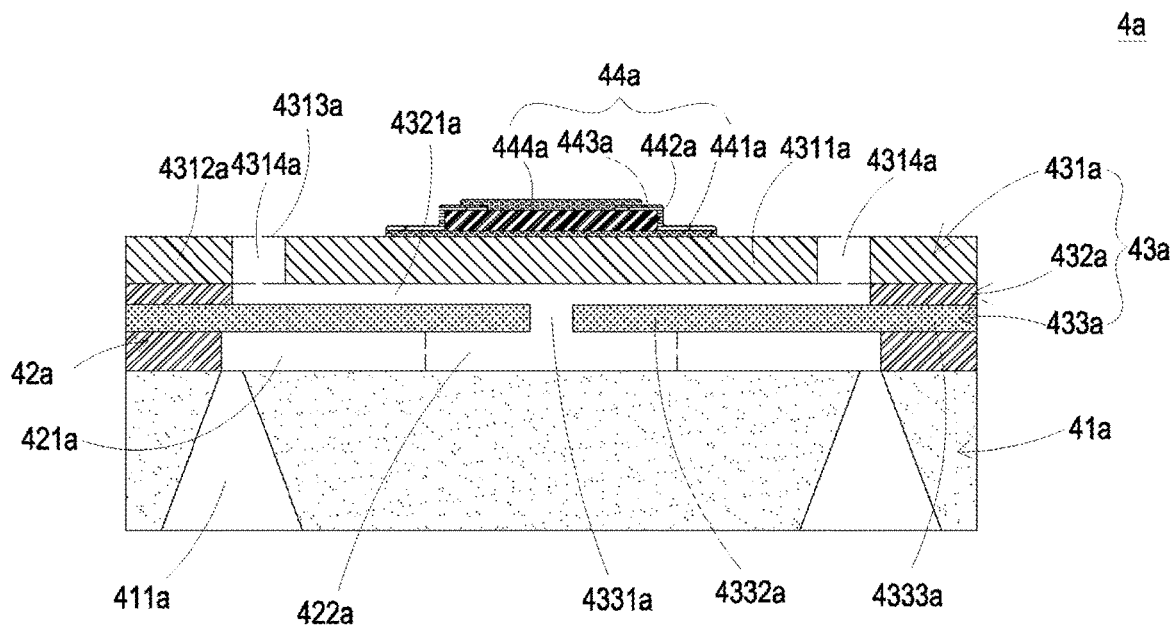
FIG. 3A illustrates a cross-sectional view of the actuation pump of the actuation air-permeable component according to an exemplary embodiment of the present disclosure.
Figure 3B:
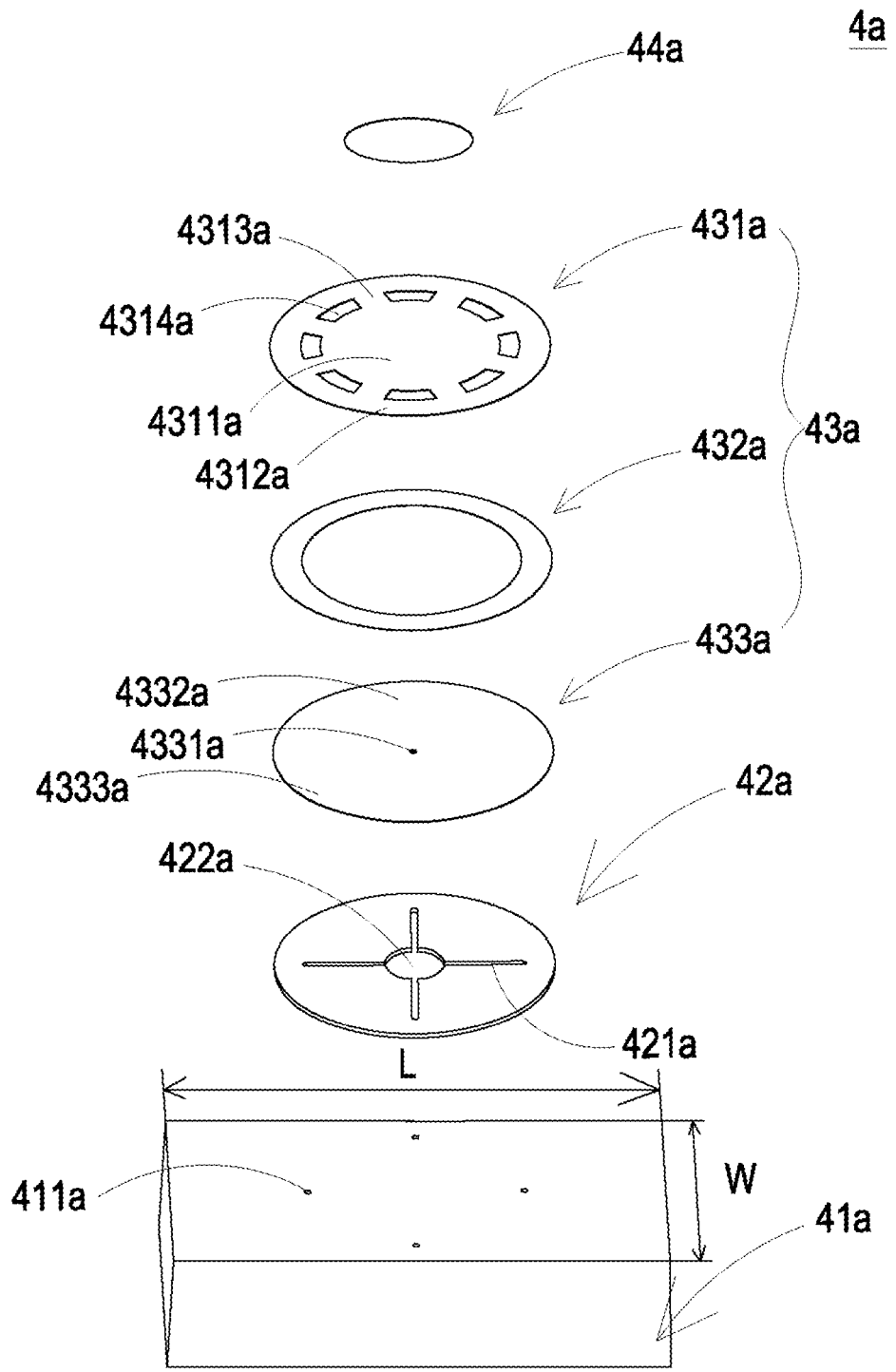
FIG. 3B illustrates an exploded view of the actuation pump of the actuation air-permeable component according to an exemplary embodiment of the present disclosure.

The actuation air-permeable components 4 woven with and positioned on the cloth body 1 comprise a plurality of actuation pumps 4a, and the actuation pumps 4a are series-connected to the microprocessor 2b of the control body 2 through the conductors A to receive the first driving signal of the microprocessor 2b and perform a gas-guiding operation. In this embodiment, the actuation air-permeable components 4 may be formed by packaging a plurality of actuation pumps 4a in a substrate B through semiconductor manufacturing processes, so that the actuation pumps 4a are series-connected to the microprocessor 2b of the control body 2 through the conductors A. In this embodiment, the substrate B is a silicon substrate. As shown in FIG. 3B, a length L of the actuation pump 4a is between 300 µm and 800 µm, and a width M of the actuation pump 4a is between 300 µm and 800 µm. In a preferred embodiment, the length L of the actuation pump 4a is between 500 µm and 700 µm, and the width M of the actuation pump 4a is between 500 µm and 700 µm. In another preferred embodiment, the length L of the actuation pump is 600 µm, and the width M of the actuation pump is 600 µm. Within the size range of the actuation pump 4a mentioned above, the actuation pump 4a can be packaged with the substrate 1 through semiconductor manufacturing processes.

The temperature sensing components 3 woven with and positioned on the cloth body 1 comprise a plurality of temperature sensors 3a, and the temperature sensors 3a are series-connected to the microprocessor 2b of the control body 2 through the conductors A, and the temperature sensors are capable of attaching to skin of a wearer to detect and generate the temperature information and output the temperature information to the microprocessor 2b. The microprocessor 2b receives and processes the temperature information to generate and provide the first driving signal to the actuation pumps 4a for performing the gas-guiding operation. In this embodiment, the temperature sensing components 3 may be formed by packaging the temperature sensors 3a in the substrate B through semiconductor manufacturing processes, so that the temperature sensors 3a are series-connected to the microprocessor 2b of the control body 2 through the conductors A. In this embodiment, the substrate B is a silicon substrate.

According to the smart cloth of one or some embodiments of the present disclosure, the temperature information of the wearer is detected by the temperature sensing components 3 and is outputted to the microprocessor 2b of the control body 2 so as to control the actuation pumps 4a of the actuation air-permeable components 4 to perform the gas-guiding operation and adjust an apparent temperature of the wearer to provide wearing comfortableness. The gas-guiding operation of the actuation pump 4a are described in the following paragraphs.

In one embodiment, the actuation pump is a microelectromechanical systems (MEMS) pump. Please refer to FIG. 3A and FIG. 3B. The MEMS pump includes a first substrate 41a, a first oxide layer 42a, a second substrate 43a, and a piezoelectric component 44a. It should be understood that in FIG. 3B, components of the MEMS pump cannot be actually taken apart since the MEMS pump is fabricated by semiconductor manufacturing processes including epitaxy, deposition, lithography, and etching. However, in order to clearly explain the detailed structure of the MEMS pump, the exploded view illustrated in FIG. 3B is used to explain the characteristics of the MEMS pump.

The first substrate 41a is a silicon wafer (Si wafer) and has a plurality of inlets 411a. In this embodiment, the number of the inlets 411a is four, but not limited thereto. Each of the inlets 411a penetrates through the first substrate 41a. Each of the inlets 411a is conical and tapered to improve the inflow efficiency of the inlets 411a.

The first oxide layer 42a is a silicon dioxide ($SiO_2$) film and is stacked on one surface of the first substrate 41a. The first oxide layer 42a has a plurality of convergence troughs 421a and a convergence chamber 422a. The number and the position of the convergence trough 421a correspond to the number and the position of the inlets 411a in the first substrate 41a. In this embodiment, the number of the convergence troughs 421a is four as well. One end of each of the four convergence troughs 421a is in communication with the corresponding inlet 411a in the first substrate 41a. The other end of each of the four convergence troughs 421a is in communication with the convergence chamber 422a. Thus, after a gas enters into the first substrate 41a from the inlets 411a, the gas flows through the convergence troughs 421a and then converges at the convergence chamber 422a.

The second substrate 43a is a silicon-on-insulator (SOI) wafer and includes a silicon wafer layer 431a, a second oxide layer 432a, and a silicon material layer 433a. The silicon wafer layer 431a has an actuation portion 4311a, an outer peripheral portion 4312a, a plurality of connection portions 4313a, and a plurality of fluid channels 4314a. The actuation portion 4311a is at a center portion of the silicon wafer layer 431a. The outer peripheral portion 4312a surrounds the periphery of the actuation portion 4311a. The connection portions 4313a are respectively located and connected between the actuation portion 4311a and the outer peripheral portion 4312a for providing flexible support. The fluid channels 4314a surround the periphery of the actuation portion 4311a is formed between the actuation portion 4311a and the outer peripheral portion 4312a and are inserted between the connection portions 4313a.

The second oxide layer 432a is made of silicon oxide and formed on the silicon wafer layer 431a. The shape of the second oxide layer 432a is a hollow ring, and the second oxide layer 432a and the silicon wafer layer 431a together define a vibration chamber 4321a. The silicon material layer 433a is firstly formed on the second oxide layer 432a and then the first oxide layer 42a is aligned with the second substrate 43a. The silicon material layer 433a is a silicon dioxide ($SiO_2$) film and has a through hole 4331a, a vibration portion 4332a, and a fixed portion 4333a. The through hole 4331a is located at a center portion of the silicon material layer 433a. The vibration portion 4332a is located at a peripheral area of the through hole 2331a and perpendicularly corresponds to the vibration chamber 4321a. The fixed portion 4333a is a peripheral area of the silicon material layer 433a and is formed on the second oxide layer 432a.

The piezoelectric component 44a is stacked on the actuation portion 4311a of the silicon wafer layer 431a and includes a lower electrode layer 441a, a piezoelectric layer 442a, an insulation layer 443a, and an upper electrode layer 444a. The lower electrode layer 441a is stacked on the actuation portion 4311a of the silicon wafer layer 431a, and the piezoelectric layer 442a is stacked on the lower electrode layer 441a. The upper electrode layer 444a and the lower electrode layer 441a are electrically connected with the piezoelectric layer 442a through the contacted area therebetween. Moreover, the width of the piezoelectric layer 442a is smaller than the width of the lower electrode layer 441a, and thus the lower electrode layer 441a is not completely covered by the piezoelectric layer 442a. The insulation layer 443a is stacked on part of the piezoelectric layer 442a and the remaining portion of the surface of the lower electrode layer 441a which is not covered by the piezoelectric layer 442a. Last, the upper electrode layer 444a is stacked on the insulation layer 443a and the remaining portion of the surface of the piezoelectric layer 442a which is not covered by the insulation layer 443a, and thus the upper electrode layer 444a is electrically connected to the piezoelectric layer 442a. Moreover, since the insulation layer 443a is inserted between the upper electrode layer 444a and the lower electrode layer 441a, a short circuit condition caused by the direct contact between the upper electrode layer 444a and the lower electrode layer 441a could be avoided.

Figure 4A:
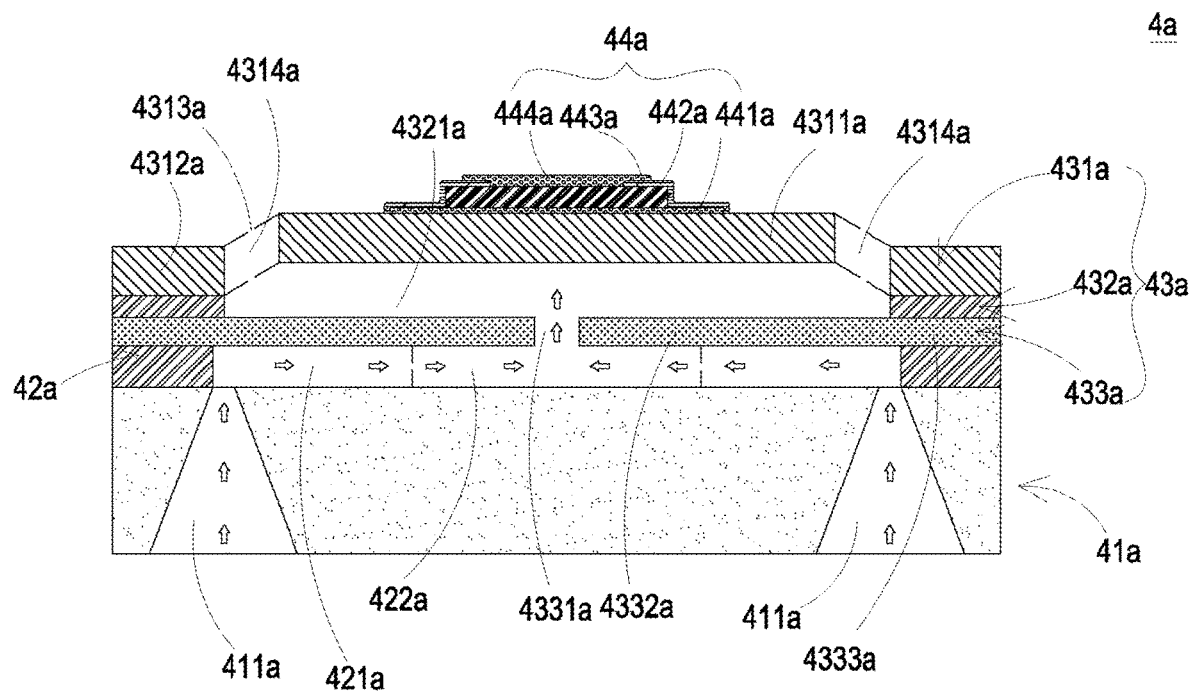
FIG. 4A to FIG. 4C illustrate schematic cross-sectional views showing the actuation pump of the actuation air-permeable component shown in FIG. 3A and FIG. 3B at different operation steps.
Figure 4B:
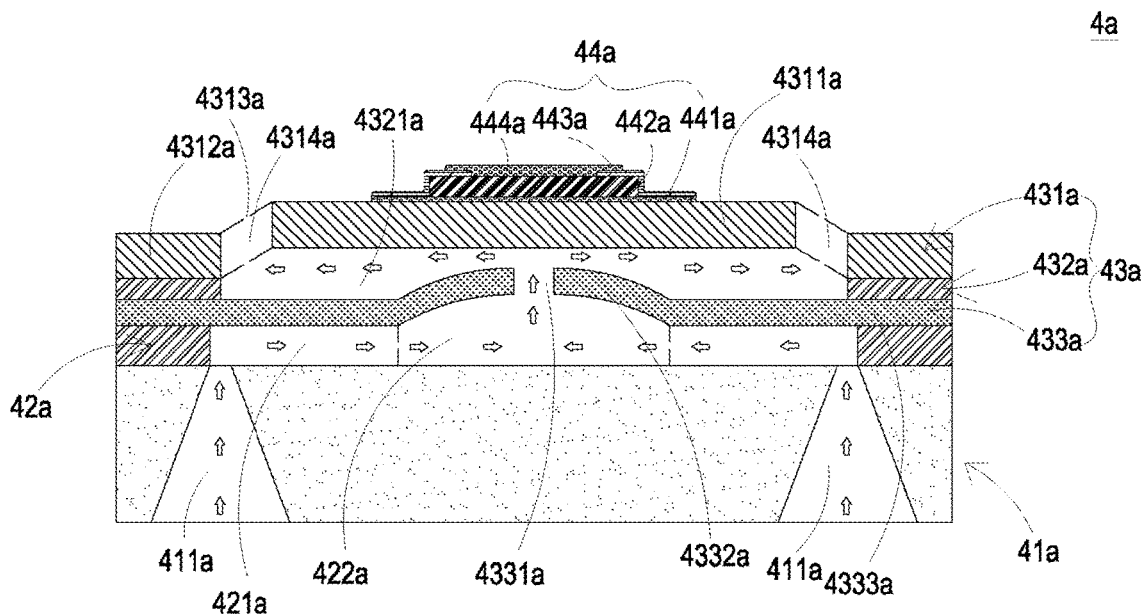
Figure 4C:
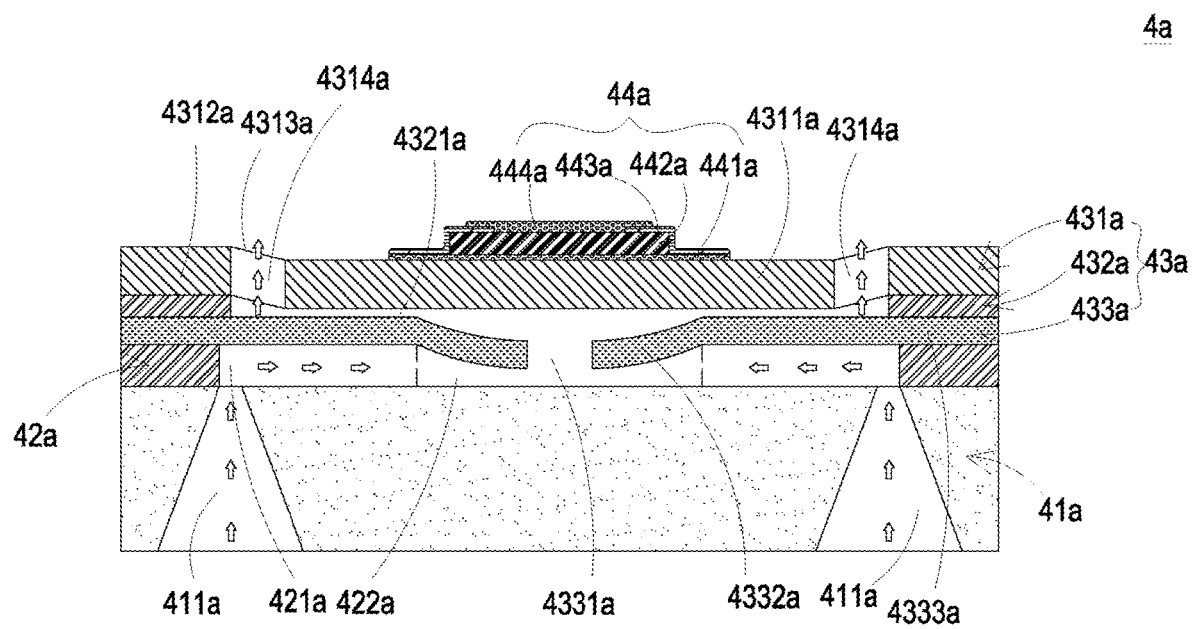

Please refer to FIG. 4A to FIG. 4C. FIG. 4A to FIG. 4C illustrate schematic cross-sectional views showing the actuation pump 4a at different operation steps. Please refer to FIG. 4A first, when the lower electrode layer 441a and the upper electrode layer 444a of the piezoelectric component 44a receive a driving signal (not shown in the figure), the piezoelectric layer 442a starts to deform because of the reverse piezoelectric effect, thereby driving the actuation portion 4311a of the silicon wafer layer 431a to move correspondingly. When the actuation portion 4311a is driven upwardly by the piezoelectric component 44a and thus the distance between the actuation portion 4311a and the second oxide layer 432a increases, the volume of the vibration chamber 4321a in the second oxide layer 432a increases as well, and a negative pressure is created in the vibration chamber 4321a as a result, and thus the gas in the convergence chamber 422a of the first oxide layer 42a is drawn into the vibration chamber 4321a through the through hole 4331a. Please refer to FIG. 4B, when the actuation portion 4311a is driven upwardly by the piezoelectric component 44a, the vibration portion 4332a of the silicon material layer 433a is moved upwardly due to the resonance effect. When the vibration portion 4332a is moved upwardly, the space of the vibration chamber 4321a is compressed and the gas in the vibration chamber 4321a is pushed to fluid channels 4314a of the silicon wafer layer 431a, so that the gas can be discharged upwardly through the fluid channels 4314a.

When the vibration portion 4332a is moved upwardly to compress the space of the vibration chamber 4321a, the volume of the convergence chamber 422a increases owing to the movement of the vibration portion 4332a and a negative pressure is created in the convergence chamber 422a, and thus the gas outside of the actuation pump 4a is drawn into the convergence chamber 422a through the inlets 411a. In the last step, as shown in FIG. 4C, when the actuation portion 4311a of the silicon wafer layer 431a is driven downwardly by the piezoelectric component 44a, the gas in the vibration chamber 4321a is pushed to the fluid channels 4314a and then discharged out. The vibration portion 4332a of the silicon material layer 433a is also driven and moved downwardly by the actuation portion 4311a and thus compresses and forces the gas in convergence chamber 422a into the vibration chamber 4321a through the through hole 4331a at the same time. Accordingly, when the actuation portion 4311a is driven upwardly by the piezoelectric component 44a again later, the volume of the vibration chamber 4321a dramatically increases, thereby generating a larger suction force to draw the gas into the vibration chamber 4321a. Trough repeating the aforementioned steps, the actuation portion 4311a can be continually driven by the piezoelectric component 44a to move upwardly and downwardly, and the vibration portion 4332a is also driven to move upwardly and downwardly correspondingly. Thus, the internal pressure of the actuation pump 4a can be changed periodically so as to draw and discharge the gas continually, thereby completing the pumping process of the actuation pump 4a.

Accordingly, the temperature sensing components 3 detect the body temperature of the wearer so as to obtain the temperature information and output the temperature information to the microprocessor 2b of the control body 2 for computation, so that the microprocessor 2b can control the actuation pumps 4a of the actuation air-permeable components 4 to perform the gas-guiding operation. Therefore, the air outside the smart cloth worn by the wearer can be guided into the cloth body 1, and the gas inside the cloth body 1 can be discharged out of the cloth body 1, thereby adjusting the apparent temperature of the wearer to provide wearing comfortableness.

Moreover, the health-monitoring device 5 woven with and positioned on the cloth body 1 includes a bio-sensing module 5a, a blood glucose sensor 5b, a blood pressure measurement module 5c, and a gas bag 5d. The bio-sensing module 5a, the blood glucose sensor 5b, and the blood pressure measurement module 5c are connected to the microprocessor 2b of the control body 2 through the conductors A. In other words, in this embodiment, the control main board 2a of the control body 2 comprises the contacts 2e, and the bio-sensing module 5a, the blood glucose sensor 5b, and the blood pressure measurement module 5c are electrically connected to the contacts 2e of the control body 2 through the conductors A so as to be further connected to the microprocessor 2b. The gas bag 5d is woven with and positioned on one of the pair of sleeves 1a of the cloth body 1. In this embodiment, the gas bag 5d is woven with and positioned on the right sleeve 1a of the cloth body 1 and the blood pressure measurement module 5c is connected to the gas bag 5d. Therefore, when the bio-sensing module 5a, the blood glucose sensor 5b, and the blood pressure measurement module 5c are attached to the skin of the wearer, the bio-sensing module 5a, the blood glucose sensor 5b, and the blood pressure measurement module 5c generate and provide the detection data information to the microprocessor 2b for output. The blood pressure measurement module 5c receives the second driving signal of the microprocessor 2b to perform the gas-guiding operation so as to inflate the gas bag 5d worn on the arm portion of the wearer, such that the blood pressure measurement module 5c could detect a blood pressure of the wearer to generate and provide the detection data information to the microprocessor 2b for output. Consequently, according to the smart cloth of one or some embodiments of the present disclosure, the bio-sensing module 5a, the blood glucose sensor 5b, and the blood pressure measurement module 5c of the health-monitoring device 5 can detect and provide the detection data information to the wearer anytime and in real-time so as to provide the health-related information to the wearer. In this embodiment, the bio-sensing module 5a is an integrated module of a photo-plethysmography (PPG) sensor and an electrocardiography (ECG) sensor and can provide a non-invasive detection. The photo-plethysmography (PPG) sensor illuminates a light beam to the skin, and detects the blood flow of the dermis and the subcutaneous tissue by measuring the change of the light refraction caused by the change of the blood flow, and generates the detection data information of heart rate data information and pulse oxygen saturation information of the health-related information. The detection data information generated by the electrocardiography sensor is electrocardiography data information of the health-related information. The detection data information generated by the blood pressure measurement 5c is blood pressure data information of the health-related information. The blood glucose sensor 5b analyzes the ingredients in the sweat of the wearer to infer the blood glucose concentration, and the detection data information generated by the blood glucose sensor 5b is blood glucose data information of the health-related information.

The operation of the blood pressure measurement of the blood pressure measurement module 5c and related components thereof are provided in detail in the following paragraphs.

Figure 5:
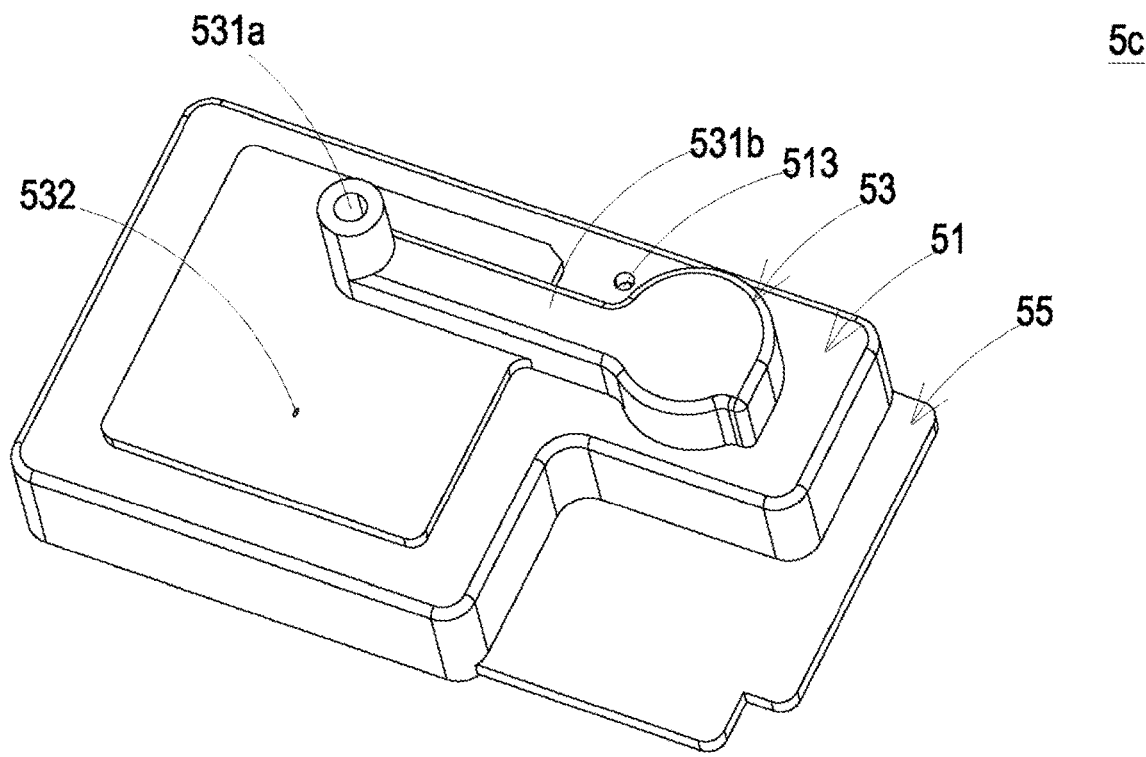
FIG. 5 illustrates a perspective view of the blood pressure measurement module of the health-monitoring device according to an exemplary embodiment of the present disclosure.
Figure 6A:
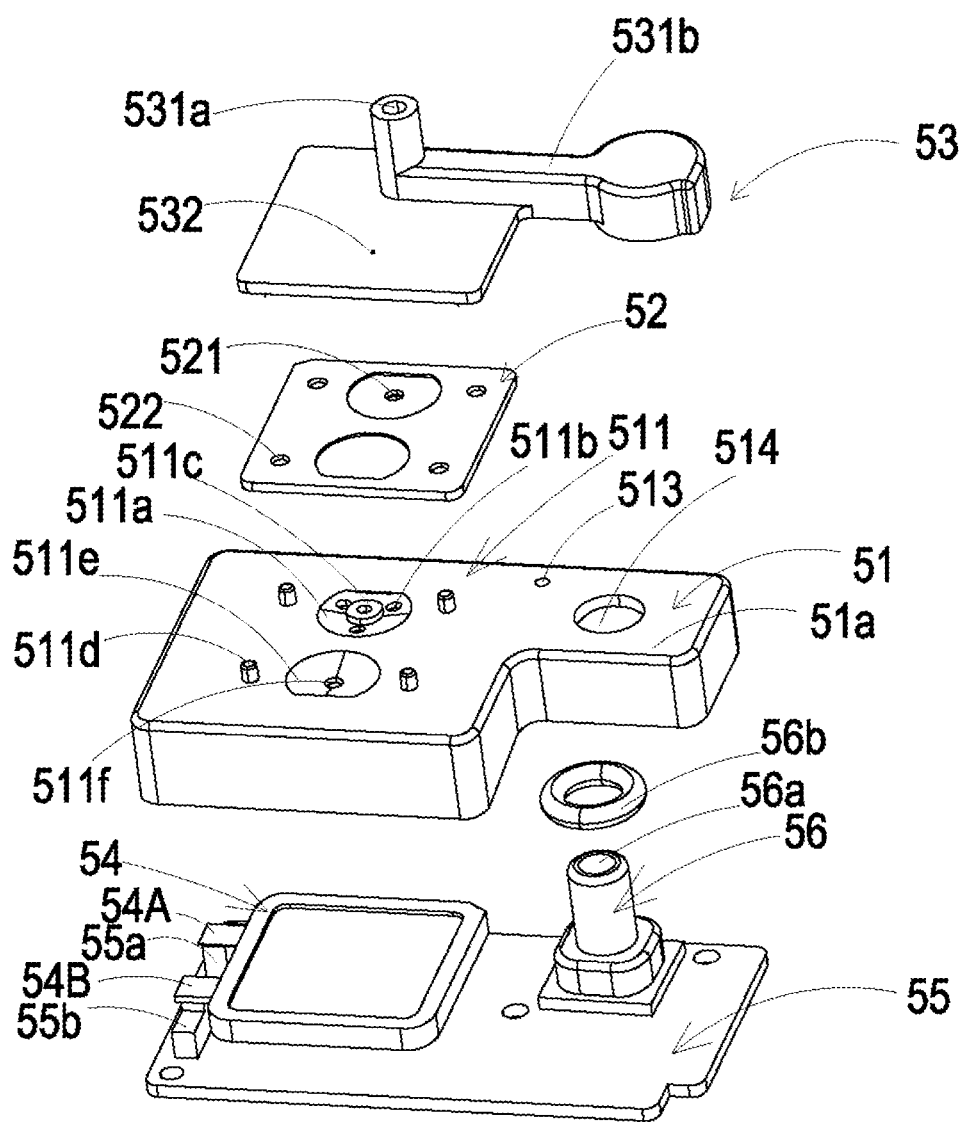
FIG. 6A illustrates an exploded view of the blood pressure measurement module of the health-monitoring device according to an exemplary embodiment of the present disclosure.
Figure 6B:
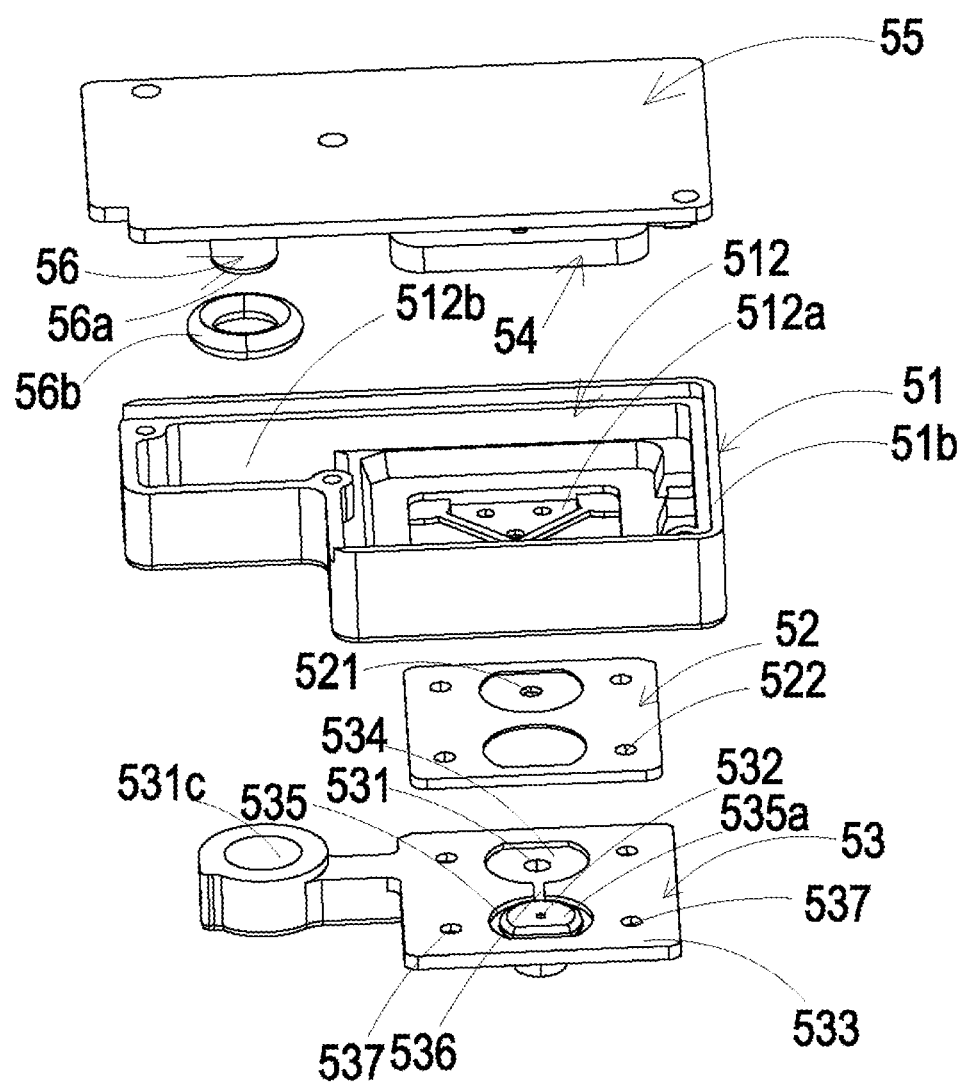
FIG. 6B illustrates an exploded view of the blood pressure measurement module of the health-monitoring device according to an exemplary embodiment of the present disclosure, from another perspective.

Please refer to FIG. 5 as well as FIG. 6A and FIG. 6B. The blood pressure measurement module 5c includes a base 51, a valve sheet 52, a top cover 53, a micro pump 54, a driving circuit board 55, and a pressure sensor 56. The base 1 is a frame-like body and includes a valve loading area 511, an accommodation trough area 512, a gas inlet hole 513, and an insertion hole 514. The valve loading area 511 is disposed on the first surface 51a of the base 51, and the accommodation trough area 12 is disposed on the second surface 51b of the base 51. The first surface 51a and the second surface 51b are opposite surfaces of the base 51. The gas inlet hole 513 and the insertion hole 514 respectively penetrate the base 51 from the first surface 51a to the second surface 51b, and the gas inlet hole 513 and the insertion hole 514 are respectively in communication with the accommodation trough area 512. The valve loading area 511 has a first recessed receiving chamber 511a, a plurality of first through holes 511b, a first protruding structure 511c, and a plurality of protruding posts 511d. The valve loading area 511 is recessed to form the first recessed receiving chamber 511a. The first protruding structure 511c extends from a center portion of the first recessed receiving chamber 511a. The first through holes 511b surround the first protruding structure 511c and penetrate the valve loading area 511. The protruding posts 511d are respectively disposed at corners of the valve loading area 511. In this embodiment, four protruding posts 511d are respectively disposed at four corners of the valve loading area 511. Moreover, the valve loading area 511 further includes a second recessed receiving chamber 511e. The second recessed receiving chamber 511e and the first recessed receiving chamber 511a are spaced apart from each other. At least one second through hole 511f penetrates an inner wall of the second recessed receiving chamber 511e, and the at least one second through hole 511f is in communication with the accommodation trough area 512. The accommodation trough area 512 comprises a gas collection chamber 512a and a sensor chamber 512b. The gas collection chamber 512a is in communication with the first through holes 511b and the at least one second through hole 511f. The configuration of the second through hole 511f increase the number of the channels between the gas collection chamber 512a and the valve loading area 511, thereby facilitating and increasing the gas transmission speed from the gas collection chamber 512a to the valve loading area 511. The sensor chamber is adjacent to one side of the gas collection chamber 512a and is in communication with the gas collection chamber 512a, and is in communication with the gas inlet hole 513 and the insertion hole 514.

Figure 8:
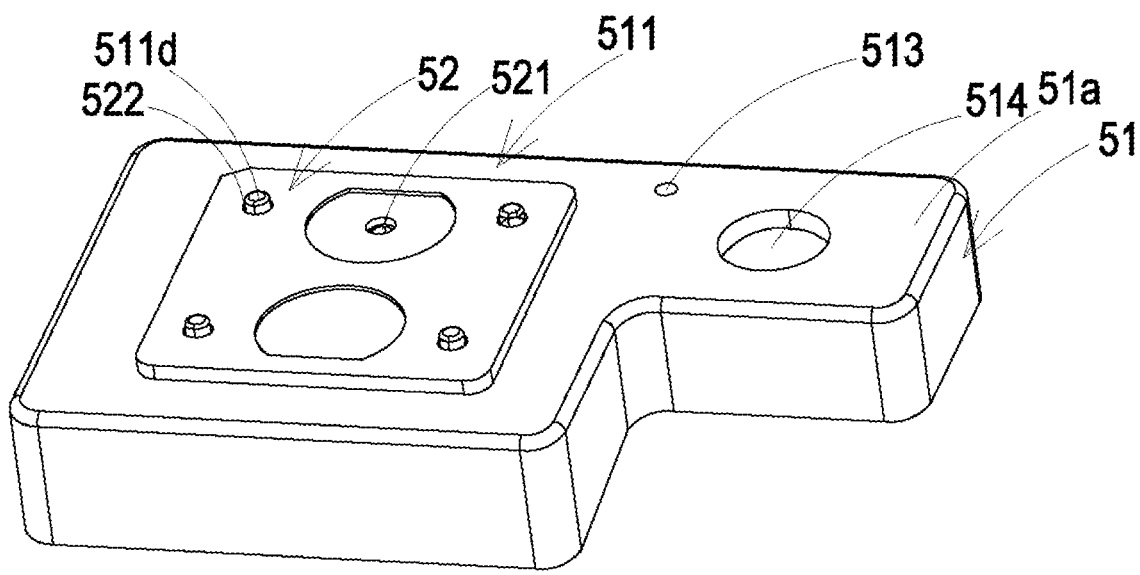
FIG. 8 illustrates a schematic view showing that the valve sheet of the blood pressure measurement module is disposed on the base according to an exemplary embodiment of the present disclosure.
Figure 11:
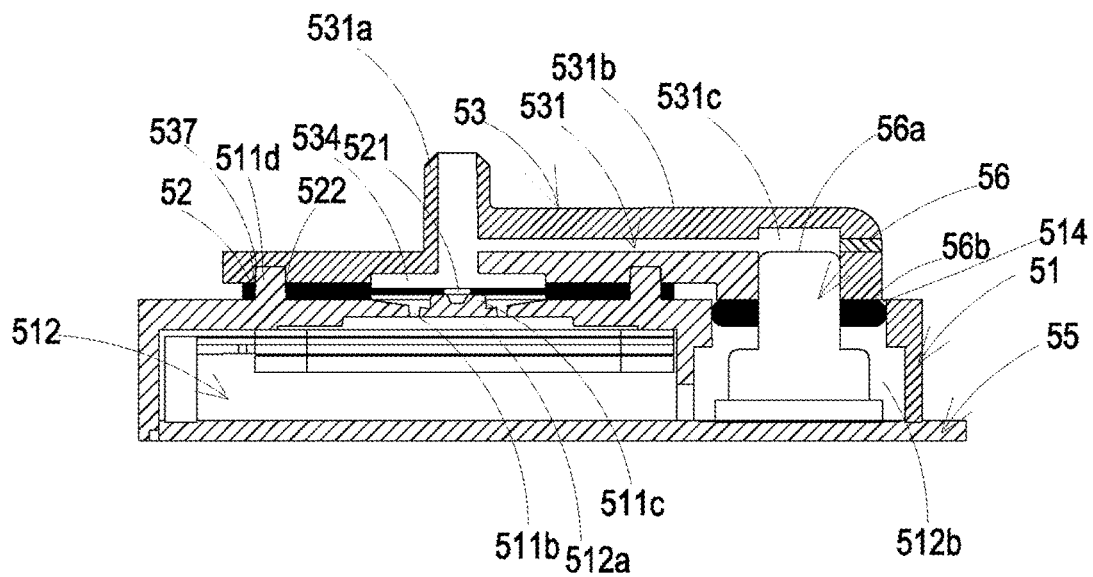
FIG. 11 illustrates a cross-sectional view of the blood pressure measurement module according to an exemplary embodiment of the present disclosure.

Please refer to FIG. 8. The valve sheet 52 is disposed on the valve loading area 511. The valve sheet 52 has a valve hole 521 and a plurality of positioning perforations 522. As shown in FIG. 11, the valve hole 521 and the first protruding structure 511c of the valve loading area 511 perpendicularly correspond to each other. The positioning perforations 522 respectively correspond to the protruding posts 511d, and the protruding posts 511d are respectively inserted into the positioning perforations 522 so as to position the valve sheet 52 on the valve loading area 511.

Figure 12A:
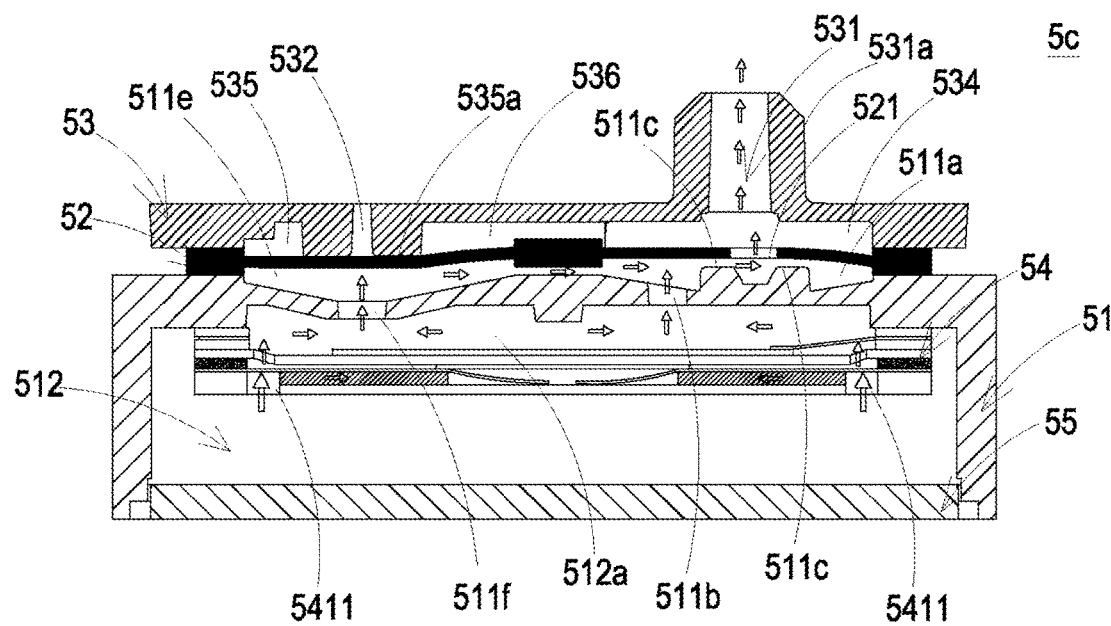
FIG. 12A illustrates a schematic view showing the gas introduction operation of the blood pressure measurement module according to an exemplary embodiment of the present disclosure.
Figure 12B:
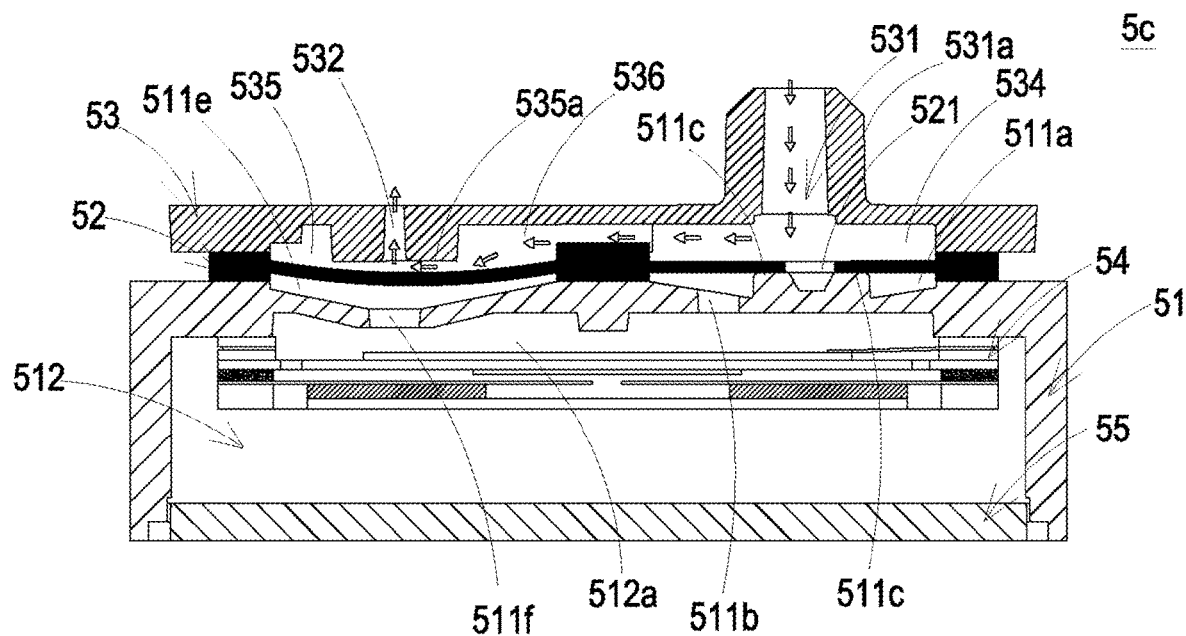
FIG. 12B illustrates a schematic view showing the gas discharge operation of the blood pressure measurement module according to an exemplary embodiment of the present disclosure.

Moreover, as shown in FIG. 5, FIG. 6B, FIG. 8, FIG. 11 as well as FIG. 12A and FIG. 12B, the top cover 53 covers the valve loading region 511 so as to seal the valve sheet 52 and the insertion hole 514. The top cover 53 has an inlet channel 531, a discharge hole 532, and an assembling surface 533. The inlet channel 531 and the discharge hole 532 are spaced apart from each other. The assembling surface 533 covers the valve sheet 52. A portion of the assembling surface 533 is recessed to form an inlet chamber 534 which is in communication with the inlet channel 531. A portion of the assembling surface 33 corresponding to the discharge hole 352 is recessed to form a discharge chamber 535. Moreover, a second protruding structure 535a protrudes from a center portion of the discharge chamber 535. The discharge hole 532 is penetrated through a center portion of the second protruding structure 535a and is in communication with the discharge chamber 535. A communication groove 536 is recessed between the inlet chamber 534 and the discharge chamber 535 so as to allow the inlet chamber 534 is in communication with the discharge chamber 535. Moreover, as shown in FIG. 3B, FIG. 10A to FIG. 10E, and FIG. 11, positioning holes 537 are located at the portions of the assembling surface 533 respectively corresponding to the protruding posts 511d of the valve loading area 511 for assembling with the protruding posts 511d.

Please refer to FIG. 5 as well as FIG. 6A and FIG. 6B. The inlet channel 531 of the top cover 53 is opposite to the assembling surface 533 and in communication with the assembling surface 533 through channels penetrated through the top cover 53. The inlet channel 531 has a connection end 531a and an extension end 531b. The connection end 531a can be connected to the gas bag 5d, and the connection end 531a is in communication with the inlet chamber 534. As shown in FIG. 5 and FIG. 11, the extension end 531b extends from the connection end 531a to correspond to the insertion hole 514, and the extension end 531b has a closing hole 531c.

Please refer to FIG. 8, FIG. 11, and FIG. 12A. The valve sheet 52 is loaded on the valve loading area 511 and is fixedly positioned between the base 51 and the top cover 53. At this time, the discharge hole 532 is at a center portion of the second protruding structure 535a, the second protruding structure 535a then abuts against the valve sheet 52 to close the discharge hole 532, thereby normally forming a pre-force action.

Please refer to FIG. 5, FIG. 6A, FIG. 6B, FIG. 11, and FIG. 12A. The micro pump 54 is disposed in the accommodation trough area 512 to cover the gas collection chamber 512a. The driving circuit board 55 covers the accommodation trough area 512, and the driving circuit board 55 is electrically connected to the micro pump 54. In this embodiment, two conductive pins 54A, 54B of the micro pump 54 are attached to soldering portions 55a, 55b of the driving circuit board 55 to have an electrical connection between the micro pump 54 and the driving circuit board 55. The driving circuit board 55 is further connected to the microprocessor 2b of the control body 2 through the conductors A, so that the driving circuit board 55 receives the second driving signal generated by the microprocessor 2b of the control body 2 and provides the micro pump 54 with the second driving signal for operation of the micro pump 54. Moreover, the pressure sensor 56 is disposed on and electrically connected to the driving circuit board 55, and the pressure sensor 56 provides the microprocessor 2b with the detection data information for output. Furthermore, the top portion of the pressure sensor 56 has a detection end 56a. When the driving circuit board 55 covers the accommodation trough area 512, the pressure sensor 56 is received in the sensor chamber 512b of the accommodation trough area 512, and the detection end 56a is inserted into the insertion hole 514 of the base 51, so that the detection end 56a is received in the closing hole 531c of the top cover 53 and the detection end 56a is in communication with the inlet channel 531. A sealing member 56b may be fitted over the detection end 56a. Therefore, the detection end 56a is inserted into the insertion hole 514 of the base 51 and received in the inlet channel 531 so as to prevent gas leakage in the inlet channel 531. Hence, when the connection end 531a of the inlet channel 531 is connected to the gas bag 5d, the detection end 56a of the pressure sensor 56 can detect the gas pressure condition inside the gas bag 5d. Accordingly, the blood pressure measurement module 5c formed by the base 51, the valve sheet 52, the top cover 53, the micro pump 54, the driving circuit board 55, and the pressure sensor 56 can be connected to the gas bag 5d. The micro pump 54 is driven by the control circuit board 55 to perform gas transmission. Therefore, the gas outside the base 51 is guided into the accommodation trough area 512 through the gas inlet hole 513, and the gas is continuously guided to and converged in the gas collection chamber 512a by the micro pump 54. The gas pushes the valve hole 521 of the valve sheet 52 so as to allow the valve sheet 52 be detached from the first protruding structure 511c, thereby the gas passing through the valve hole 521 so as to be continuously guided into the inlet channel 531 of the top cover 53 and collected in the gas bag 5d, whereby the gas inflates the gas bag 5d to press the arm of the wearer. The gas pressure condition inside the gas bag 5d can be detected by the pressure sensor 56, so that the detection data information about the blood pressure of the wearer is detected and calculated by the pressure sensor 56. Then, the microprocessor 2b outputs a notification of the detection data information about the blood pressure of the wearer.

The descriptions of detail features and operations of the micro pump 54 of the blood pressure measurement module 5c are provided in the following paragraphs.

Figure 7:
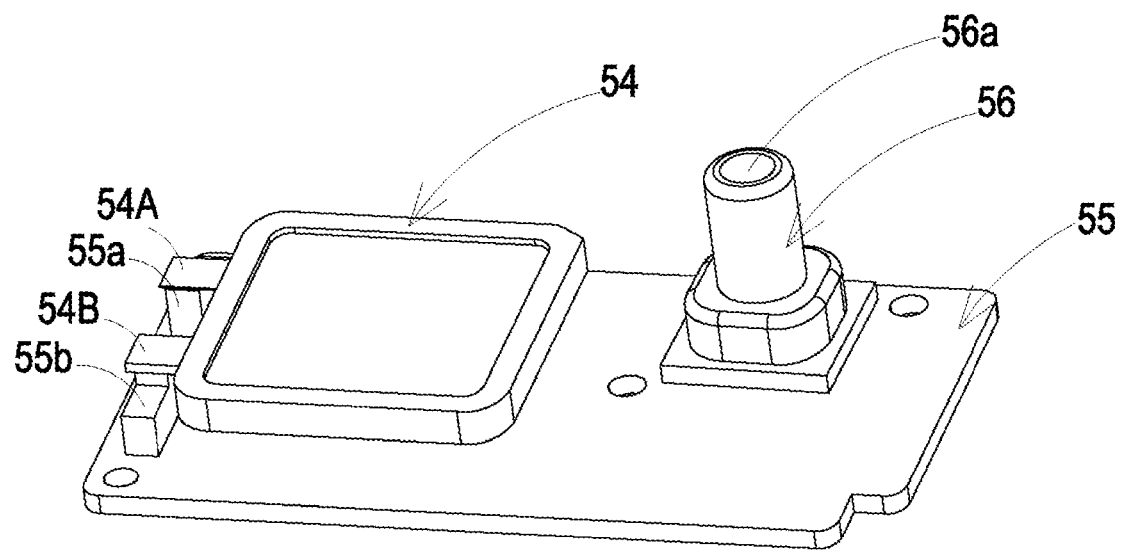
FIG. 7 illustrates a schematic view showing that the pressure sensor of the blood pressure measurement module is disposed on the driving circuit board according to an exemplary embodiment of the present disclosure.
Figure 9A:
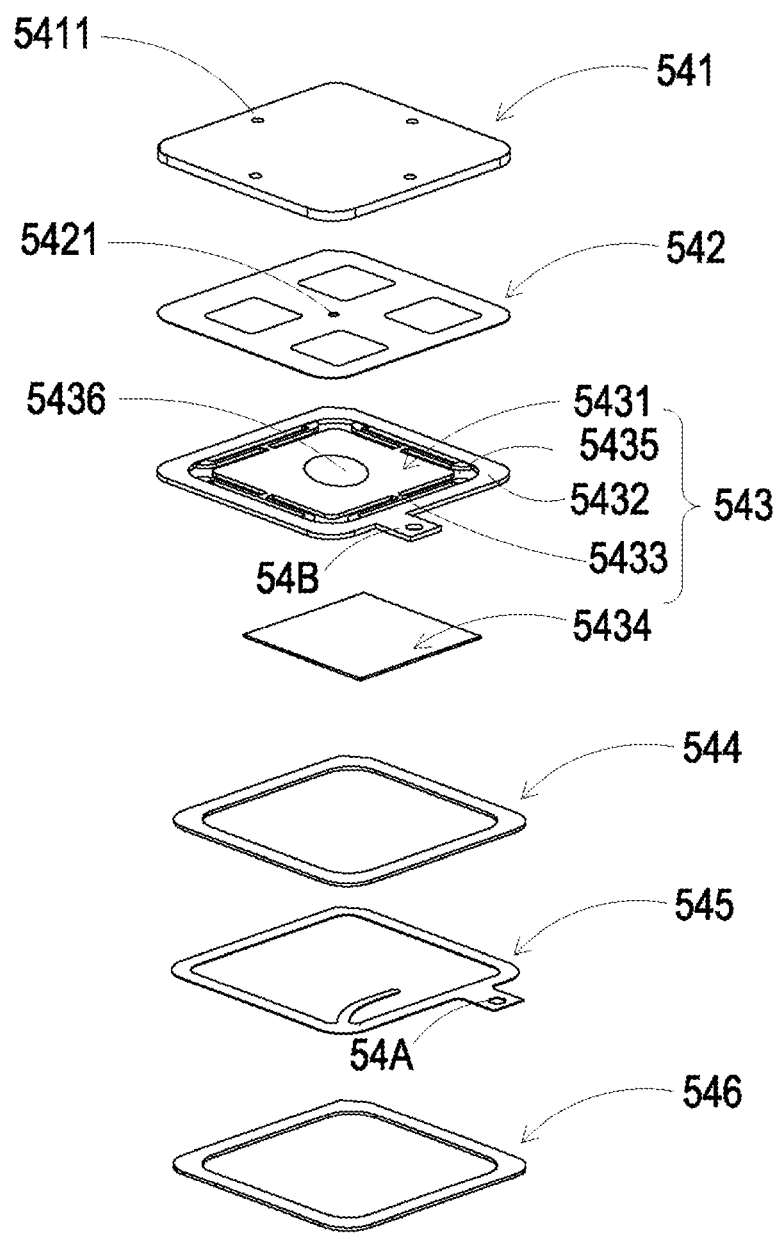
FIG. 9A illustrates an exploded view of the micro pump of the blood pressure measurement module according to an exemplary embodiment of the present disclosure.
Figure 9B:
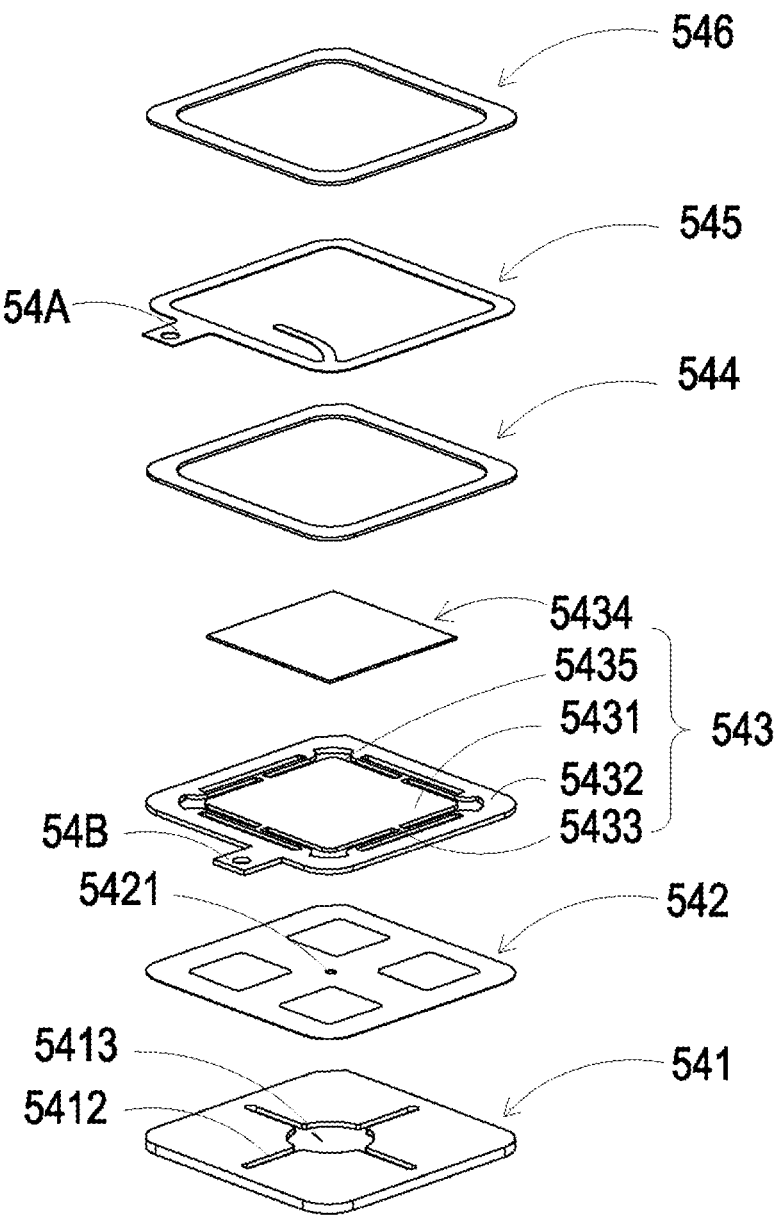
FIG. 9B illustrates an exploded view of the micro pump of the blood pressure measurement module according to an exemplary embodiment of the present disclosure, from another perspective.

Please refer to FIG. 9A and FIG. 9B as well as FIG. 10A to FIG. 10E. The micro pump 54 includes an inlet plate 541, a resonance sheet 542, a piezoelectric actuator 543, a first insulation sheet 544, a conductive sheet 545, and a second insulation sheet 546. The piezoelectric actuator 543 is disposed correspondingly to the resonance sheet 542. The inlet plate 541, the resonance sheet 542, the piezoelectric actuator 543, the first insulation sheet 544, the conductive sheet 545, and the second insulation sheet 546 are sequentially stacked and assembled with each other. Moreover, the conductive sheet 545 has a conductive pin 54A extending outwardly, and the piezoelectric actuator 543 has a conductive pin 54B extending outwardly, the conductive pins 54A, 54B are respectively attached to the soldering portions 55a, 55b of the driving circuit board 55 to have an electrical connection between the micro pump 54 and the driving circuit board 55 (as shown in FIG. 7), so that the driving circuit board 55 can control the operation of the micro pump 54.

The inlet plate 541 has at least one inlet hole 5411, at least one convergence trough 5412, and a convergence chamber 5413. In this embodiment, the number of the inlet holes 5411 is preferably four, but not limited thereto. The inlet hole 5411 penetrates the inlet plate 541, so that the gas outside the micro pump 54 can flow into the micro pump 54 from the inlet hole 5411 in response to the atmospheric pressure. The inlet plate 541 has the at least one convergence trough 5412, and the number and the position of the convergence trough 5412 is corresponding to that of the inlet hole 5411 on the opposite side of the inlet plate 541. In the present embodiment, the number of the inlet holes 5411 are four, and the number of the convergence troughs 5412 are four as well. The convergence chamber 5413 is at the center portion of the inlet plate 541. One end of each of the four convergence troughs 5412 is connected to the corresponding inlet hole 5411, and the other end of each of the four convergence troughs 5412 is connected to the convergence chamber 5413 at the center portion of the inlet plate 541. Therefore, the gas can be guided to the convergence chamber 5413 from the inlet holes 5411 via the convergence troughs 5412. In this embodiment, the inlet hole 5411, the convergence trough 5412, and the convergence chamber 5413 are integrally formed in the inlet plate 541.

The resonance sheet 542 has a perforation 5421 corresponding to the convergence chamber 5413 of the inlet plate 541 for the gas to pass therethrough, and a movable portion 5422 is provided around the perforation 5421. The piezoelectric actuator 543 is disposed correspondingly to the resonance sheet 542. The piezoelectric actuator 543 is assembled by a suspension plate 5431, an outer frame 5432, at least one supporting element 5433, and a piezoelectric element 5434, and the piezoelectric actuator 543 has a conductive pin 54B. The suspension plate 5431 has a square shape and is capable of bending and vibrating. The outer frame 5432 is disposed around the periphery of the suspension plate 5431, and the supporting element 5433 is connected between the suspension plate 5431 and the outer frame 5432 to provide a flexible support for the suspension plate 5431. The piezoelectric element 5434 also has a square shape and is attached to one surface of the suspension plate 5431 so as to drive the suspension plate 5431 to bend and vibrate when the piezoelectric element 5434 is applied with a voltage. The side length of the piezoelectric element 5434 is smaller than or equal to a side length of the suspension plate 5431. A plurality of gaps 5435 is formed between the suspension plate 5431, the outer frame 5432, and the supporting element 5433 for the gas to pass therethrough. Moreover, the piezoelectric actuator 543 has a protruding portion 5436 disposed on the other surface of the suspension plate 5431. That is, the piezoelectric element 5434 and the protruding portion 5436 are respectively disposed on the two opposite surfaces of the suspension plate 5431.

Figure 10A:
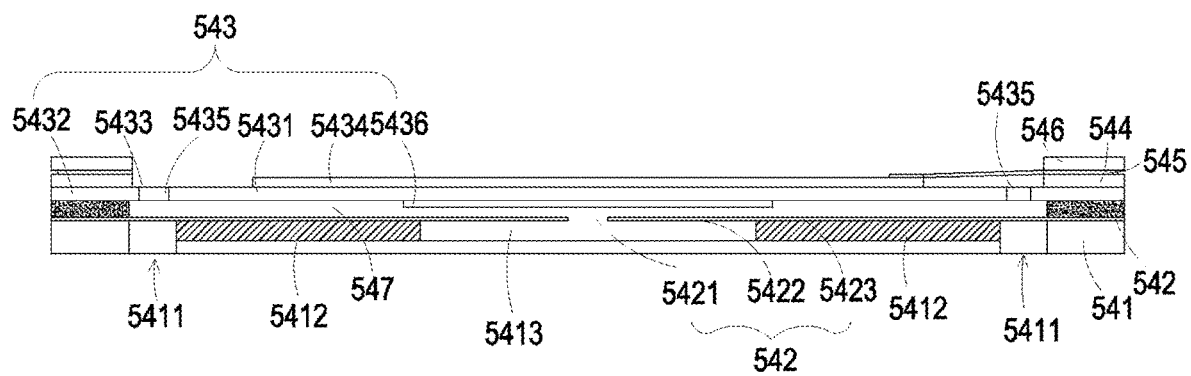
FIG. 10A illustrates a cross-sectional view of the micro pump of the blood pressure measurement module according to an exemplary embodiment of the present disclosure.

As shown in FIG. 10A, in some embodiments, the inlet plate 541, the resonance sheet 542, the piezoelectric actuator 543, the first insulation sheet 544, the conductive sheet 545, and the second insulation sheet 546 are stacked sequentially with each other. The thickness of the suspension plate 5431 of the piezoelectric actuator 543 is smaller than the thickness of the outer frame 5432. Thus, when the resonance sheet 542 is stacked on the piezoelectric actuator 543, a chamber space 547 can be formed between the suspension plate 5431 of the piezoelectric actuator 543, the outer frame 5432, and the resonance sheet 542.

Figure 10B:
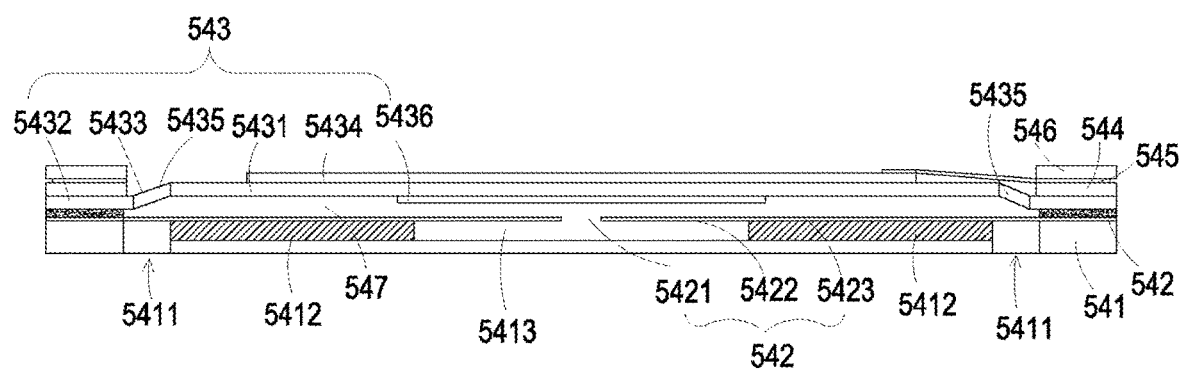
FIG. 10B illustrates a cross-sectional view of the micro pump of the blood pressure measurement module according to an exemplary embodiment of the present disclosure, from another perspective.

Please refer to FIG. 10B. FIG. 10B shows another embodiment of the micro pump 54. Most of the elements in FIG. 10B are similar to the corresponding elements in FIG. 10A, and will not be reiterated here. One difference between the embodiment shown in FIG. 10B and the embodiment shown in FIG. 10A resides in that, in FIG. 10B, when the micro pump 54 does not actuate, the suspension plate 5431 of the piezoelectric actuator 543 extends away from the resonance sheet 542 by stamping, so that the suspension plate 5431 and the outer frame 5432 are not aligned at the same level. The extended distance of the suspension plate 5431 may be adjusted by the supporting elements 5433. In such embodiments, the supporting elements 5433 are not parallel to the suspension plate 5431, so that a part of the piezoelectric actuator 543 has a convex profile.

Figure 10C:
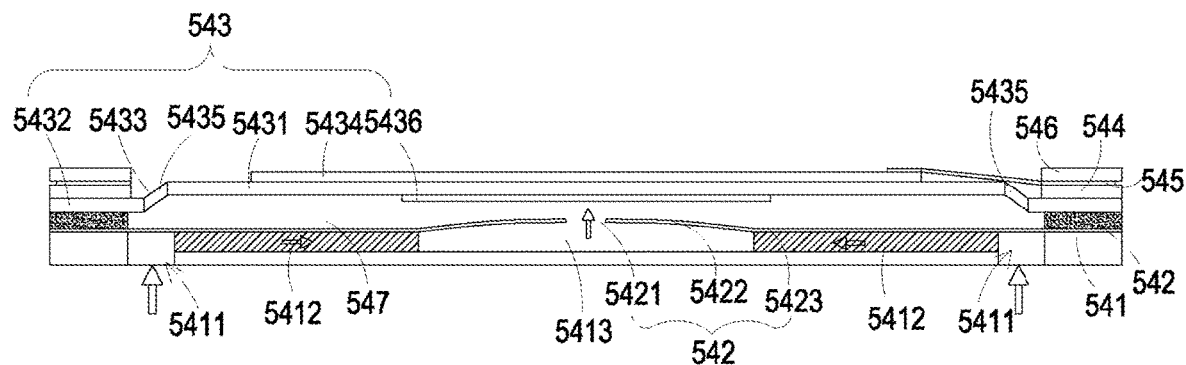
FIG. 10C to FIG. 10E illustrate schematic cross-sectional views showing the micro pump shown in FIG. 10A and FIG. 10B at different operation steps.
Figure 10D:
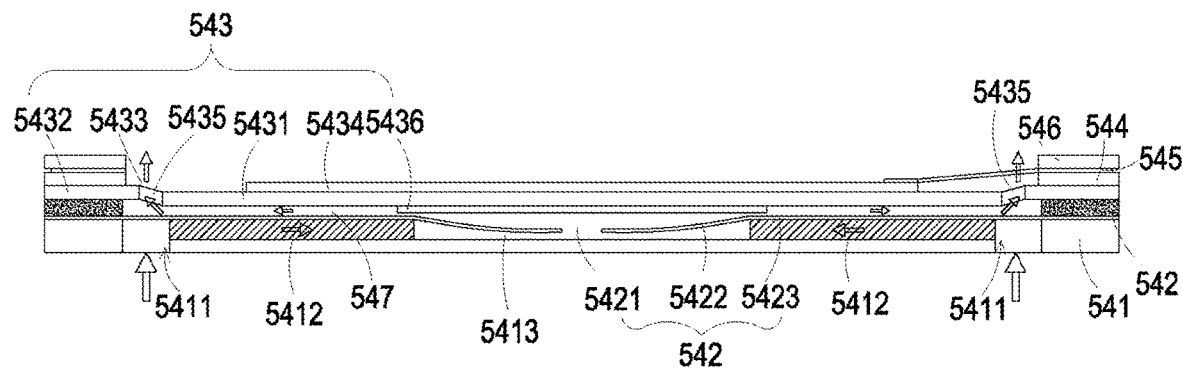
Figure 10E:
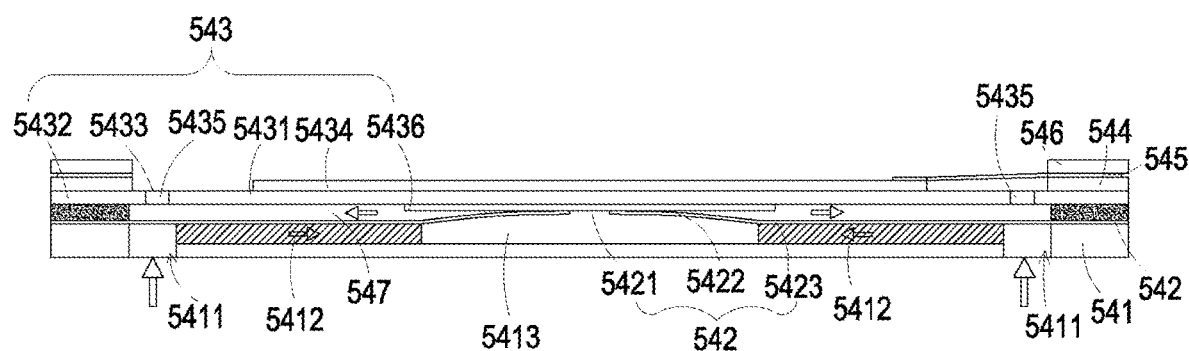

In order to understand the operation of the aforementioned micro pump 54 in transmitting gas, please refer to FIG. 10C to FIG. 10E. Please refer to FIG. 10C first, the piezoelectric element 5434 of the piezoelectric actuator 543 deforms after being applied with a driving voltage, and the piezoelectric element 5434 drives the suspension plate 5431 to move upwardly. Thus, the volume of the chamber space 547 is increased and a negative pressure is generated inside the chamber space 547, thereby drawing the gas in the convergence chamber 5413 into the chamber space 547. At the same time, owing to the resonance effect, the movable portion 5422 of the resonance sheet 542 is correspondingly bent and moved upwardly, which also increases the volume of the convergence chamber 5413. Furthermore, since the gas inside the convergence chamber 5413 is drawn into the chamber space 547, the convergence chamber 5413 is in a negative pressure state as well. Therefore, the gas can be drawn into the convergence chamber 5413 through the inlet hole 5411 and the convergence trough 5412. Then, please refer to FIG. 10D. The piezoelectric element 5434 drives the suspension plate 5431 to move downwardly, thereby compressing the chamber space 547. Similarly, since the resonance sheet 542 resonates with the suspension plate 5431, the resonance sheet 542 also moves downwardly, thereby pushing the gas in the chamber space 547 to be upwardly transmitted out of the micro pump 54 through the at least one gap 5435. At last, please refer to FIG. 10E, When the suspension plate 5431 moves resiliently to its original position, the resonance sheet 542 still moves downwardly due to its inertia momentum. At the time, the resonance sheet 542 compresses the chamber space 547, so that the gas in the chamber space 547 is moved toward the gap 5435 and the volume of the convergence chamber 5413 is increased. Accordingly, the gas can be drawn into the convergence chamber 5413 continuously through the inlet holes 5411 and the convergence channels 5412 and can be converged at the convergence chamber 5413. Through continuously repeating the operation steps of the micro pump 54 shown in FIG. 10C to FIG. 10E, the micro pump 54 can make the gas continuously enter into the flow paths formed by the inlet plate 541 and the resonance sheet 542 from the inlet holes 5411, thereby generating a pressure gradient. The gas is then transmitted outward through the gap 5435. As a result, the gas can flow at a relatively high speed, thereby achieving the effect of gas transmission of the micro pump 54.

Based on above description, when the blood pressure measurement module 5c of the health-monitoring device 5 is connected to the gas bag 5d, the gas bag 5d can be inflated to press the arm portion of the wearer, and the gas pressure condition inside the gas bag 5d can be detected by the pressure sensor 56. Therefore, the blood pressure of the wearer can be detected, calculated and measured. It is understood that, the microprocessor 2b of the control body 2 provides the second driving signal for the blood pressure measurement module 5c so as to drive the micro pump 54 of the blood pressure measurement module 5c for gas transmission, so that the pressure sensor 56 can detect the gas pressure inside the gas bag 5d. The requirement of measuring blood pressure of the wearer may include generating a trend information of detection data by the pressure sensor 56 in a period of time, and the period of time may be one or several days, one or several weeks, one or several months, or one or several years.

Please refer to FIG. 1 and FIG. 2. The smart cloth may further include a gas detection module 6 packaged with and electrically connected to the control main board 2a of the control body 2 so as to detect the gas outside the cloth body 1 to generate gas data information and transmits the gas data information to the microprocessor 2b, so as to allow the microprocessor 2b to transmits the gas data information to the external device 7 through the communication device 2d for alerting and notifying.

Figure 13A:
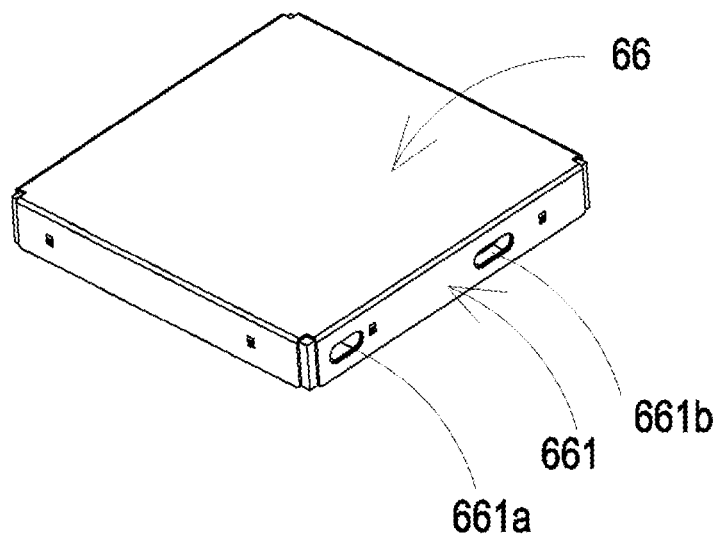
FIG. 13A illustrates a perspective view of the gas detection module according to an exemplary embodiment of the present disclosure.
Figure 13B:
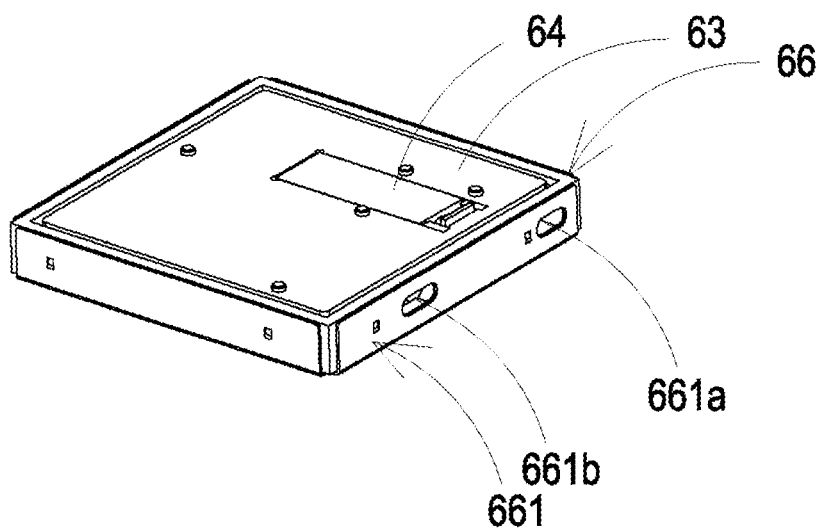
FIG. 13B illustrates a perspective view of the gas detection module according to an exemplary embodiment of the present disclosure, from another perspective.
Figure 13C:
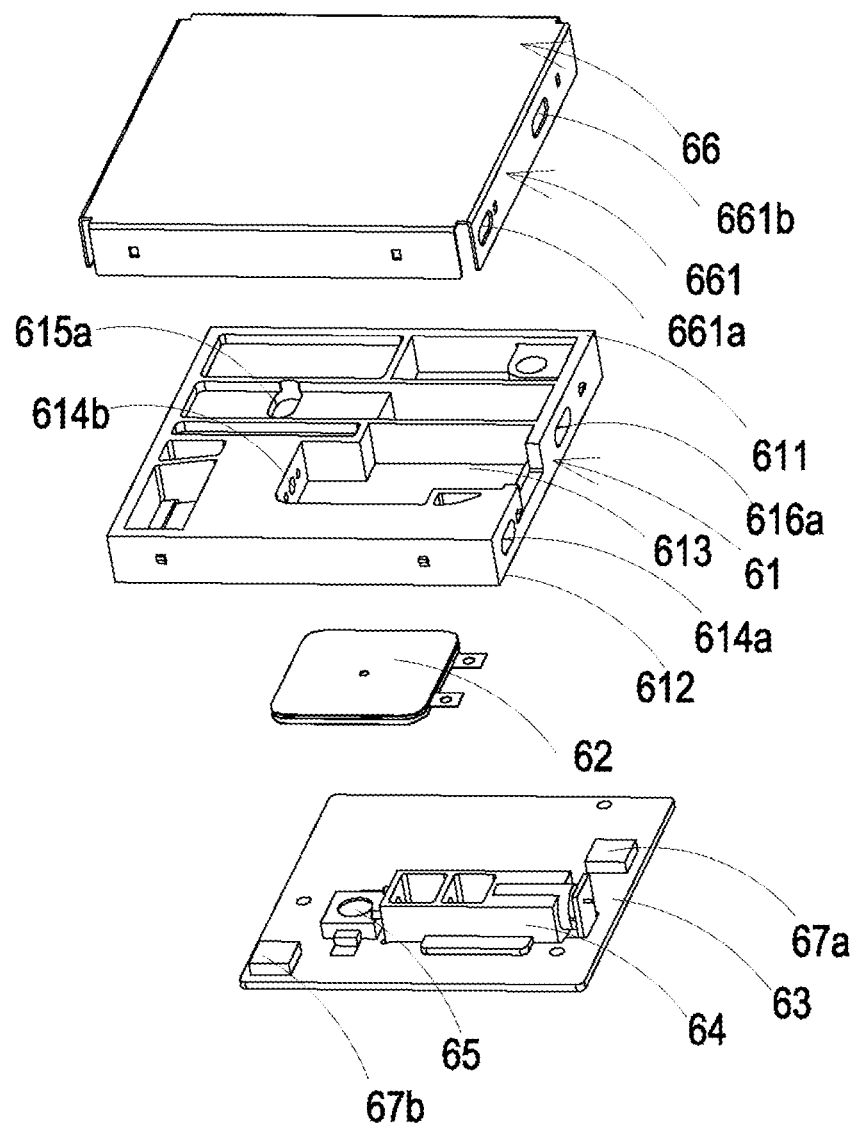
FIG. 13C illustrates an exploded view of the gas detection module according to an exemplary embodiment of the present disclosure.
Figure 14A:
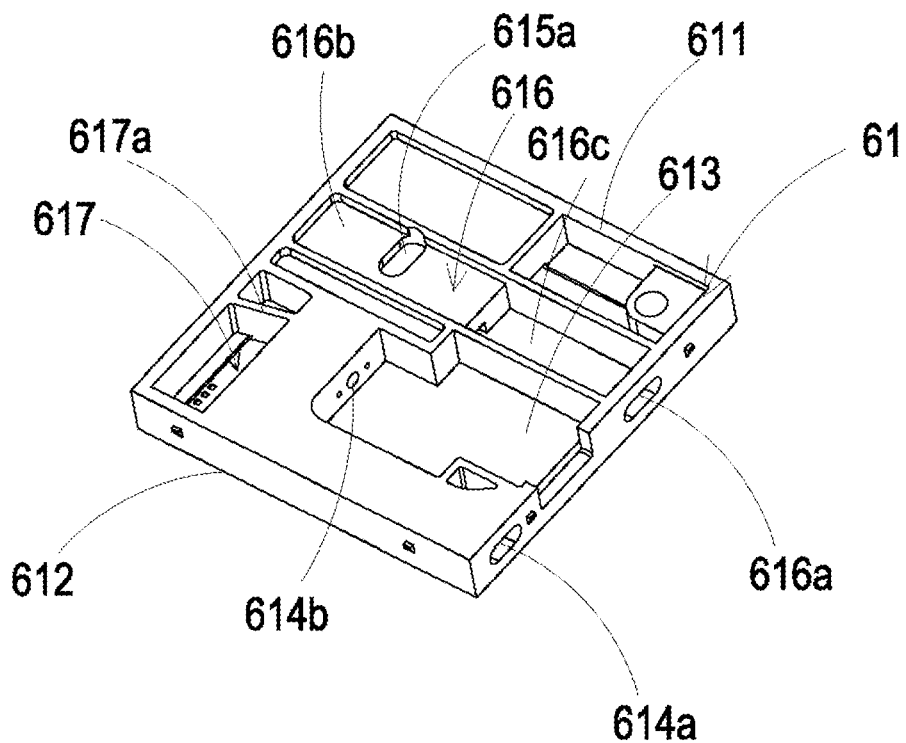
FIG. 14A illustrates a perspective view of the module body of the gas detection module according to an exemplary embodiment of the present disclosure.
Figure 14B:
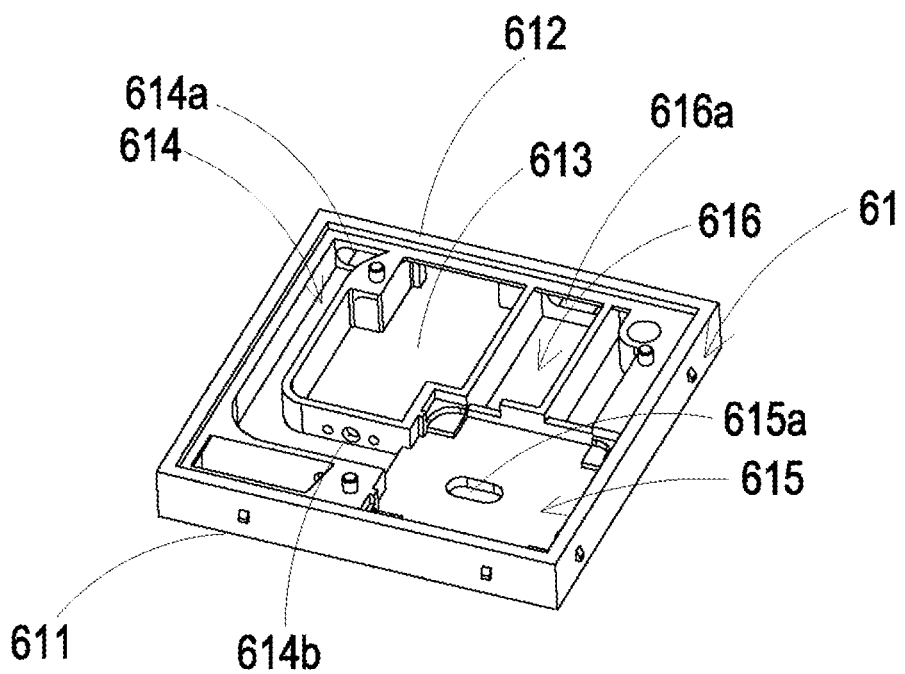
FIG. 14B illustrates a perspective view of the module body of the gas detection module according to an exemplary embodiment of the present disclosure. from another perspective.
Figure 15:
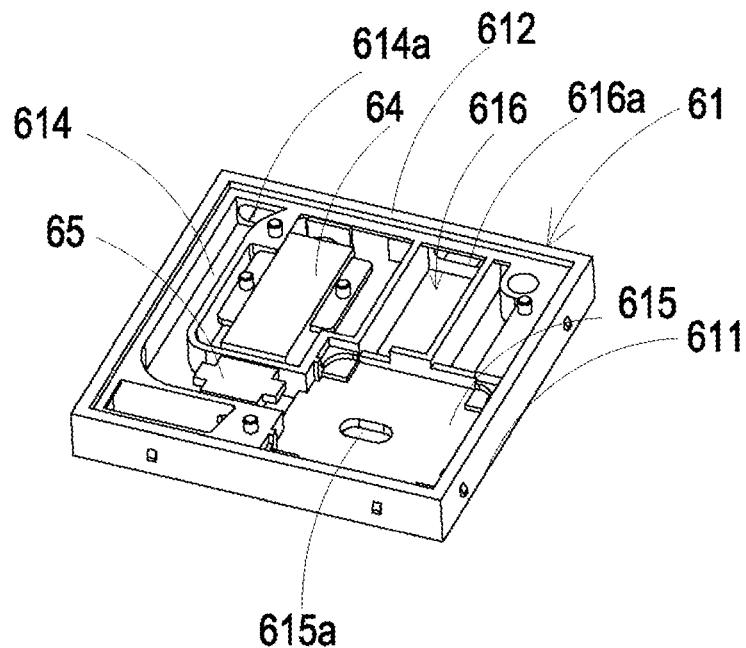
FIG. 15 illustrates a perspective view showing that the laser component and the particulate sensor are received in the module body of the gas detection module according to an exemplary embodiment of the present disclosure.
Figure 19A:
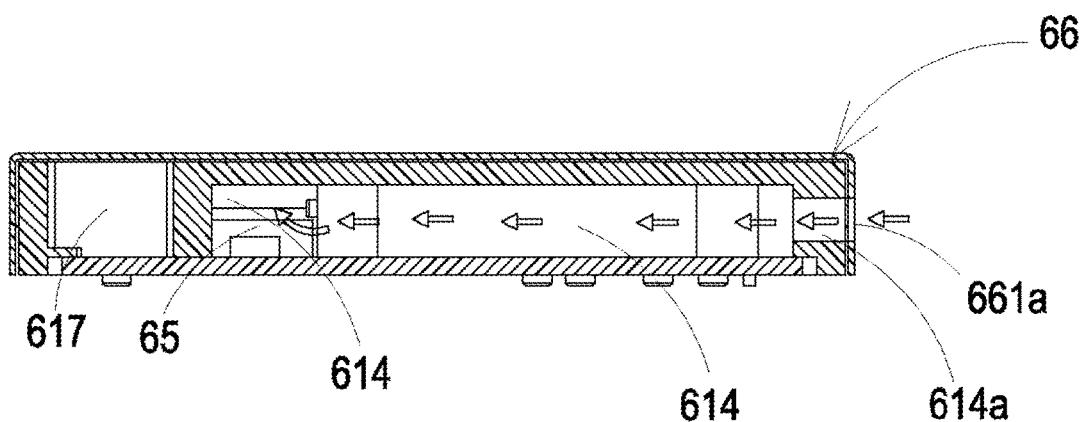
FIG. 19A to FIG. 19C illustrate schematic cross-sectional views showing the gas paths of the gas detection module according to an exemplary embodiment of the present disclosure.

Further, as shown in FIG. 13A to 13C, FIG. 14A and FIG. 14B, FIG. 15, and FIG. 16A and FIG. 16B, the gas detection module 6 includes a module body 61, a micro flow-guiding pump 62, a module driving board 63, a laser component 64, a particulate sensor 65, and an outer cap 66. As shown in FIG. 14A and FIG. 14B, the module body 61 has a first surface 611, a second surface 612, a laser configuration region 613, a gas inlet groove 614, a gas-guiding component loading region 615, and a gas outlet groove 616. The first surface 611 and the second surface 612 are opposite surfaces. The laser configuration region 613 is hollowed out from the first surface 611 to the second surface 612. The gas inlet groove 614 is recessed from the second surface 612 and located adjacent to the laser configuration region 613. The gas inlet groove 614 has a gas inlet through hole 614a and two lateral walls, and the gas inlet through hole 614a is in communication with outside of the module body 61. Moreover, as shown in FIG. 13A and FIG. 13B, the outer cap 66 has a side plate 661, and the side plate 661 has a gas inlet opening 661a and a gas outlet opening 661b. Therefore, when the outer cap 66 covers the module body 61, the gas inlet through hole 614a is corresponding to the gas inlet opening 661a of the outer cap 66. Furthermore, as shown in FIG. 14A and FIG. 14B, a light permissive window 614b is opened on and ran through the lateral wall of the gas inlet groove 614 and is in communication with the laser configuration region 613. Therefore, the first surface 611 of the module body 61 is covered by the outer cap 66, and the second surface 612 of the module body 61 is covered by the driving circuit board 63, so that the gas inlet groove 614 defines a gas inlet path (as shown in FIG. 15 and FIG. 19A).

Figure 19B:
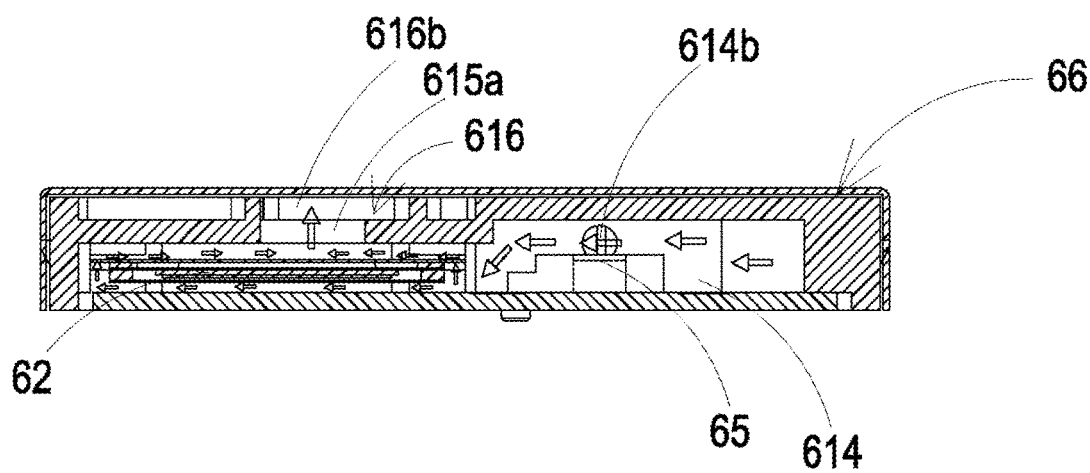
Figure 19C:
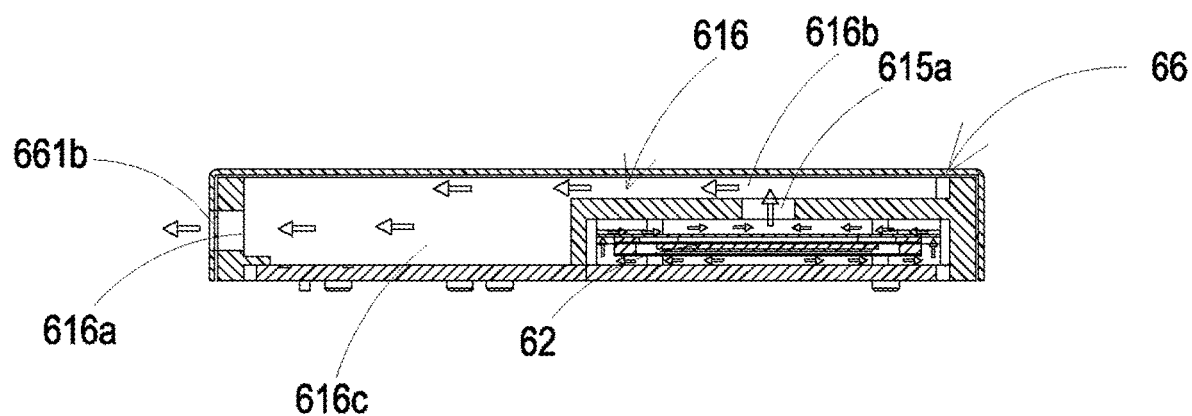

Furthermore, as shown in FIG. 14A and FIG. 14B, the gas-guiding component loading region 615 is recessed from the second surface 612 and in communication with the gas inlet groove 614. A gas flowing hole 615a penetrates a bottom surface of the gas-guiding component loading region 615. The gas outlet groove 616 has a gas outlet through hole 616a corresponding to the gas outlet opening 661b of the outer cap 66. The gas outlet groove 616 includes a first region 616b and a second region 616c. The first region 616b is recessed from a portion of the first surface 611 corresponding to a vertical projection region of the gas-guiding component loading region 615. The second region 616c is located at a portion extending from a portion not included in the vertical projection region of the gas-guiding component loading region 615, and the second region 616c is hollowed out from the first surface 611 to the second surface 612. The first region 616b is connected to the second region 616c to form a stepped structure. Moreover, the first region 616b of the gas outlet groove 616 is in communication with the gas flowing hole 615a of the gas-guiding component loading region 615, and the second region 616c of the gas outlet groove 616 is in communication with the gas outlet through hole 616a. Therefore, the first surface 611 of the module body 61 is covered by the outer cap 66, and the second surface 612 of the module body 61 is covered by the driving circuit board 63, so that the gas outlet groove 616 defines a gas outlet path (as shown in FIG. 15 and FIG. 19C).

Furthermore, as shown in FIG. 13C and FIG. 15, the laser component 64 and the particulate sensor 65 are disposed on the driving circuit board 63 and located in the module body 61. Here, in order to clearly explain the positions of the laser component 64, the particulate sensor 65, and the module body 61, the driving circuit board 63 is not illustrated in FIG. 15. Please refer to FIG. 13C, FIG. 14B, and FIG. 15. The laser component 64 is received in the laser configuration region 613 of the module body 61. The particulate sensor 65 is received in the gas inlet groove 614 of the module body 61 and aligned with the laser component 64. Moreover, the laser component 64 is corresponding to the light permissive window 614b. The light beam emitted by the laser component 64 to pass through the light permissive window 614b so as to allow the light beam to further enter into the gas inlet groove 614. The path of the light beam emitted by the laser component 64 passes through the light permissive window 614b and is orthogonal to the gas inlet groove 614. The light beam emitted by the laser component 64 enters into the gas inlet groove 614 through the light permissive window 614b, and the particulate contained in the gas in the gas inlet groove 614 are illuminated by the light beam. When the light beam encounters the particulate, the light beam scatters and generates light spots. Hence, the particulate sensor 65 receives and calculates the light spots generated by the scattering, such that the particulate sensor 65 obtains the information regarding to the particle size and the concentration of the particulate in the gas and other related information. The particulate may include viruses and bacteria. The particulate sensor 65 may be a PM2.5 sensor.

Figure 16A:
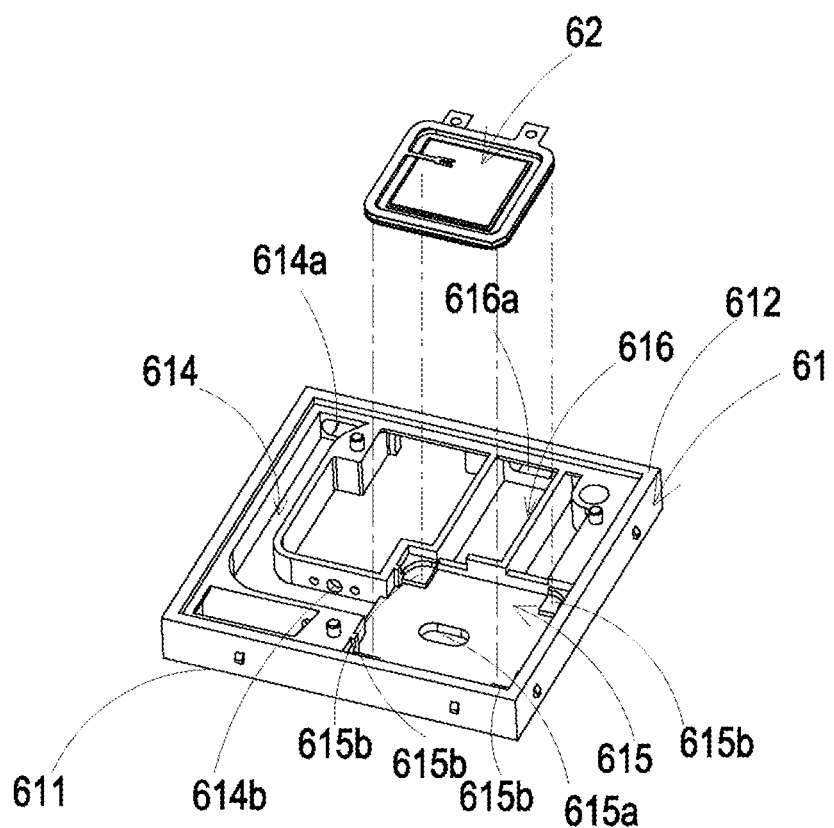
FIG. 16A illustrates an exploded view showing that the micro flow-guiding pump of the gas detection module is to be assembled with the module body according to an exemplary embodiment of the present disclosure.
Figure 16B:
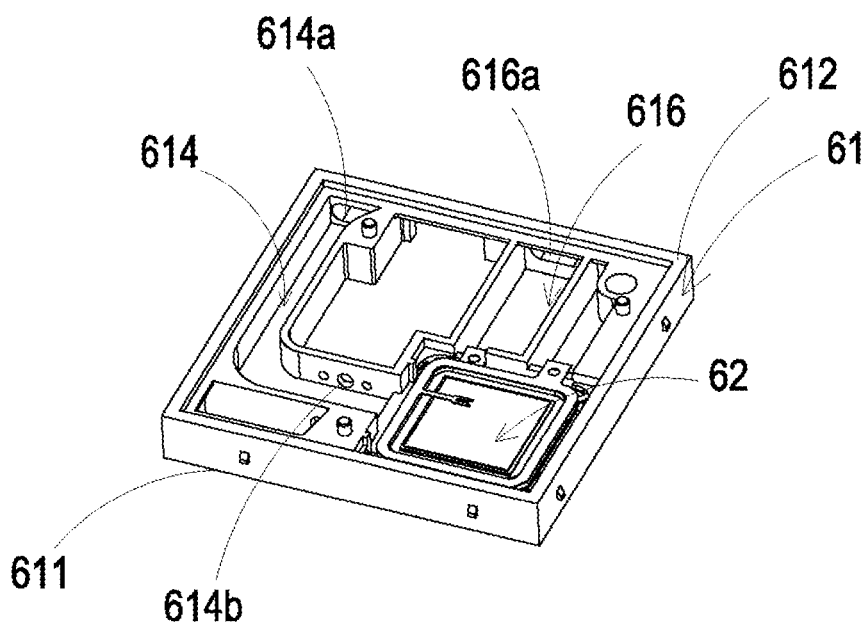
FIG. 16B illustrates a perspective view showing that the micro flow-guiding pump of the gas detection module is assembled with the module body according to an exemplary embodiment of the present disclosure.

Furthermore, as shown in FIG. 16A and FIG. 16B, the micro flow-guiding pump 62 is received in the gas-guiding component loading region 615 of the module body 61. The shape of the gas-guiding component loading region 615 is square, and each of the four corners of the gas-guiding component loading region 615 has a positioning bump 615b. The micro flow-guiding pump 62 is disposed in the gas-guiding component loading region 615 by the four positioning bumps 615b. Furthermore, as shown in FIG. 17A, FIG. 17B, FIG. 19B, and FIG. 19C, the gas-guiding component loading region 615 is in communication with the gas inlet groove 614. When the micro flow-guiding bump 62 operates, the gas in the gas inlet groove 614 is drawn into the micro flow-guiding bump 62, and the gas passes through the gas flowing hole 615a of the gas-guiding component loading region 615 and enters into the gas outlet groove 616.

Furthermore, as shown in FIG. 1, FIG. 2, FIG. 13B and FIG. 13C, the module driving board 63 is packaged with and electrically connected to the control main board 2a of the control body 2, and the micro flow-guiding pump 62 is packaged with and electrically connected to the control main board 2a of the control body 2, so that the module driving board 63 receives a third driving signal generated by the microprocessor 2b to perform the gas-guiding operation. Moreover, the module driving board 63 covers the second surface 612 of the module body 61. The laser component 64 is disposed on and electrically connected to the module driving board 63. The particulate sensor 65 is also disposed on and electrically connected to the module driving board 63. Moreover, as shown in FIG. 13A, the gas inlet opening 661a is corresponding to the gas inlet through hole 614a of the module body 61 (as shown in FIG. 19A), and the gas outlet opening 661b is corresponding to the gas outlet through hole 616a of the module body 61 (as shown in FIG. 19C), as the outer cap 66 covers the module body 61.

Figure 17A:
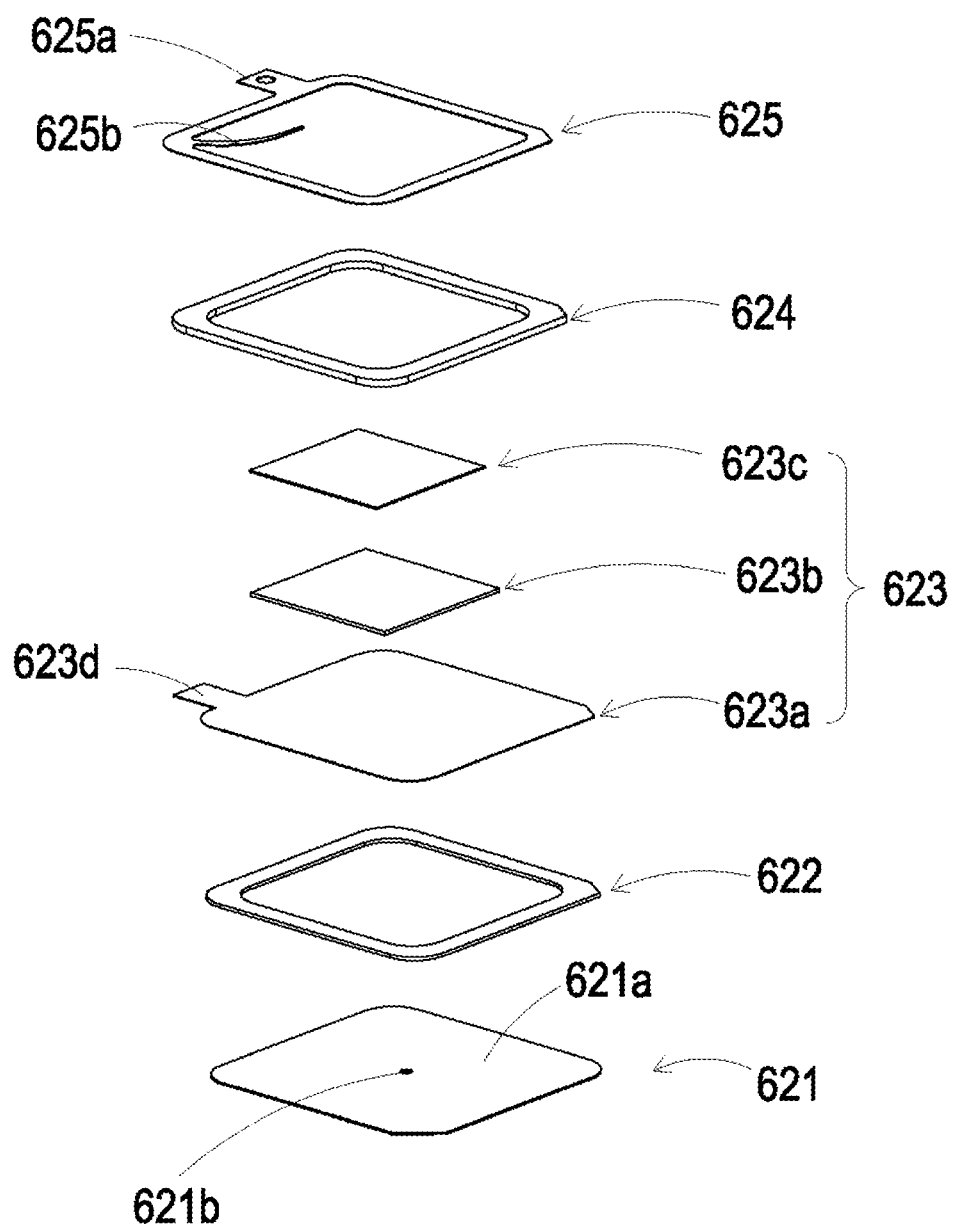
FIG. 17A illustrates an exploded view of the micro flow-guiding pump of the gas detection module according to an exemplary embodiment of the present disclosure.
Figure 17B:
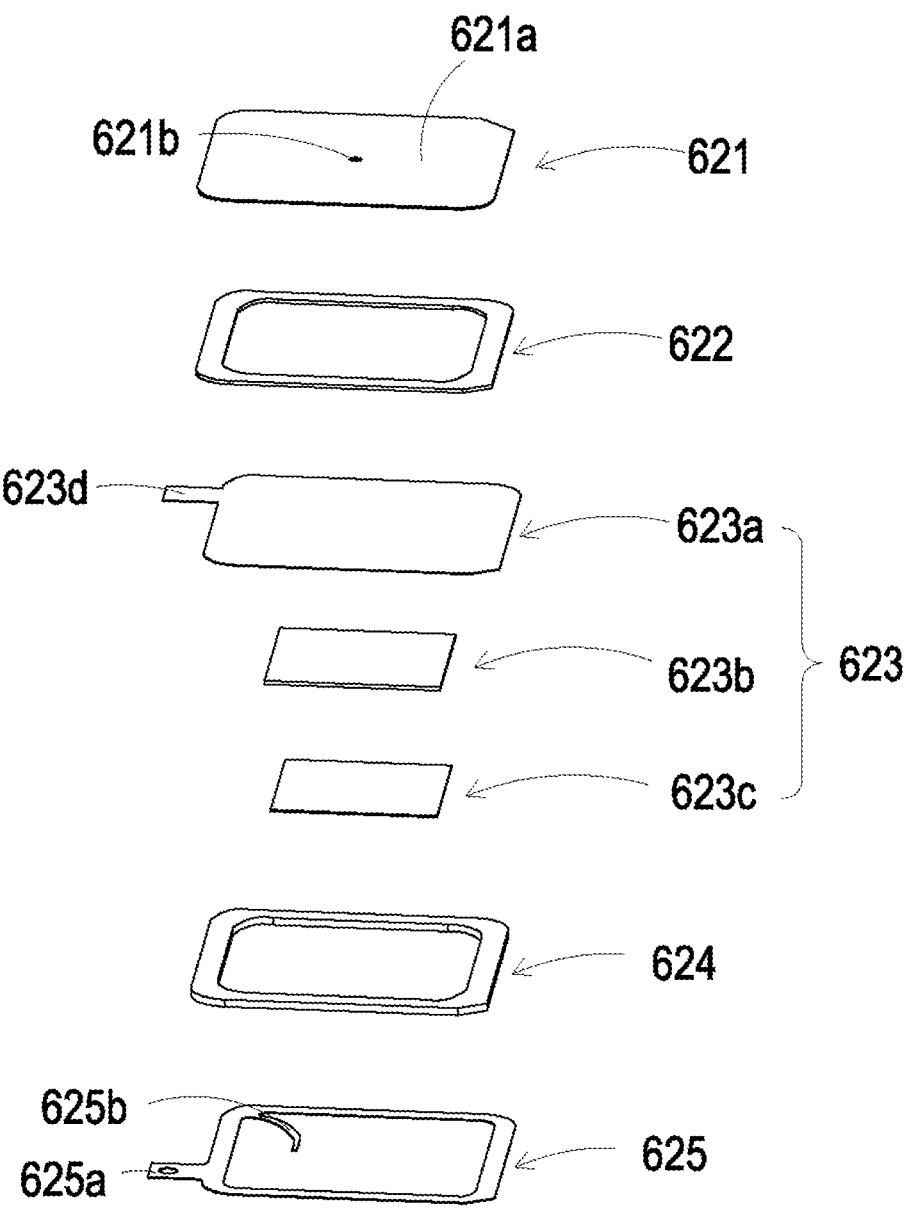
FIG. 17B illustrates an exploded view of the micro flow-guiding pump of the gas detection module according to an exemplary embodiment of the present disclosure, from another perspective.

Please refer to FIG. 17A and FIG. 17B. The micro flow-guiding pump 62 includes a nozzle plate 621, a chamber frame 622, an actuation body 623, an insulation frame 624, and a conductive frame 625. The nozzle plate 621 is made of a flexible material and has a suspension sheet 621a and a hollow hole 621b. The suspension sheet 621a is a flexible sheet, which can bend and vibrate. The shape and the size of the suspension sheet 621a are approximately corresponding to those of the inner edge of the gas-guiding component loading region 615, but not limited thereto. The shape of the suspension sheet 621a may be one of square, circle, ellipse, triangle, and polygon. The hollow hole 621b penetrates the center portion of the suspension sheet 621a for allowing the gas to flow therethrough.

Figure 18A:
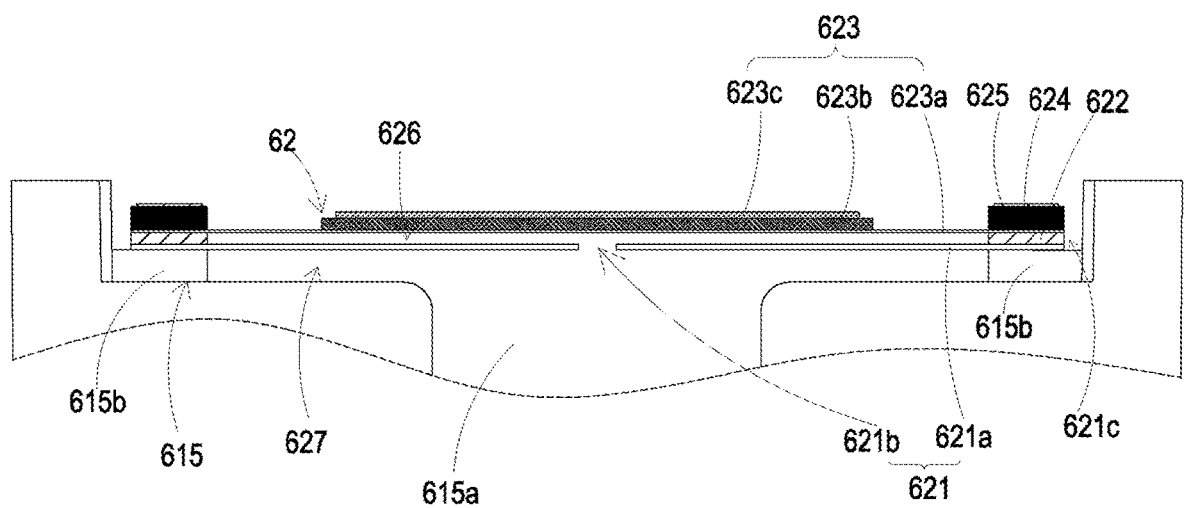
FIG. 18A illustrates a cross-sectional view showing that the micro flow-guiding pump of the gas detection module is assembled with the gas-guiding component loading region according to an exemplary embodiment of the present disclosure.

As shown in FIG. 17A, FIG. 17B, and FIG. 18A. The chamber frame 622 is stacked on the nozzle plate 621, and the shape of the chamber frame 622 is corresponding to the shape of the nozzle plate 621. The actuation body 623 is stacked on the chamber frame 622, and a resonance chamber 626 is formed between the chamber frame 622, the actuation body 623, and the suspension sheet 621a. The insulation frame 624 is stacked on the actuation body 623, and the appearance of the insulation frame 624 is similar to that of the chamber frame 622. The conductive frame 625 is stacked on the insulation frame 624, and the appearance of the conductive frame 625 is similar to that of the insulation frame 624. The conductive frame 625 has a conductive frame pin 625a and a conductive electrode 625b. The conductive frame pin 625a extends outwardly from the outer edge of the conductive frame 625, and the conductive electrode 625b extends inwardly from the inner edge of the conductive frame 625. Moreover, the actuation body 623 further includes a piezoelectric carrier plate 623a, an adjusting resonance plate 623b, and a piezoelectric plate 623c. The piezoelectric carrier plate 623a is stacked on the chamber frame 622. The adjusting resonance plate 623b is stacked on the piezoelectric carrier plate 623a. The piezoelectric plate 623c is stacked on the adjusting resonance plate 623b. The adjusting resonance plate 623b and the piezoelectric plate 623c are accommodated in the insulation frame 624. The conductive electrode 625b of the conductive frame 625 is electrically connected to the piezoelectric plate 623c. The piezoelectric carrier plate 623a and the adjusting resonance plate 623b are both made of the conductive materials. The piezoelectric carrier plate 623a has a piezoelectric pin 623d. The piezoelectric pin 623d and the conductive frame pin 625a are electrical connected with the module driving board 63 (not shown) so as to receive the third driving signal. The piezoelectric pin 623d, the piezoelectric carrier plate 623a, the adjusting resonance plate 623b, the piezoelectric plate 623c, the conductive electrode 625b, the conductive frame 625, and the conductive frame pin 625a may together form a circuit for transmitting the third driving signal, and the insulation frame 624 is provided for electrically isolating the conductive frame 625 and the actuation body 623 for avoiding short circuit, thereby the third driving signal can be transmitted to the piezoelectric plate 623c. When the piezoelectric plate 623c receives the third driving signal, the piezoelectric plate 623c deforms owing to the piezoelectric effect, and thus the piezoelectric carrier plate 623a and the adjusting resonance plate 623b are driven to perform reciprocating vibration correspondingly.

As mentioned above, the adjusting resonance plate 623b is disposed between the piezoelectric plate 623c and the piezoelectric carrier plate 623a. As a result, the adjusting resonance plate 623b can be served as a cushion element between the piezoelectric plate 623c and the piezoelectric carrier plate 623a, by which the vibration frequency of the piezoelectric carrier plate 623a can be adjusted. Generally, the thickness of the adjusting resonance plate 623b is greater than the thickness of the piezoelectric carrier plate 623a. The thickness of the adjusting resonance plate 623b may be changed so as to adjust the vibration frequency of the actuation body 623.

Please refer to FIG. 17A, FIG. 17B, and FIG. 18A. The nozzle plate 621, the chamber frame 622, the actuation body 623, the insulation frame 624, and the conductive frame 625 are sequentially stacked and assembled with each other and are disposed in the gas-guiding component loading region 615, so that the micro flow-guiding pump 62 is placed and positioned in the gas-guiding component loading region 615. Moreover, the micro flow-guiding pump is fixed on the positioning bumps 615b through the nozzle plate 621, so that the micro flow-guiding pump 62 defines a surrounding gap 621c between the suspension sheet 621a and the inner edge of the gas-guiding component loading region 615 for the gas to pass therethrough.

Please refer to FIG. 17A first. A gas flow chamber 627 is formed between a bottom of the nozzle plate 621 and the bottom surface of the gas-guiding component loading region 615. The gas flow chamber 627 is in communication with, through the hollow hole 621b of the nozzle plate 621, the resonance chamber 626 formed between the actuation body 623, the chamber frame 622, and the suspension sheet 621a. By controlling the vibration frequency of the gas in the resonance chamber 626 to be close to the vibration frequency of the suspension sheet 621a, the resonance chamber 626 and the suspension sheet 621a can generate the Helmholtz resonance effect so as to improve the transmission efficiency of the gas.

Figure 18B:
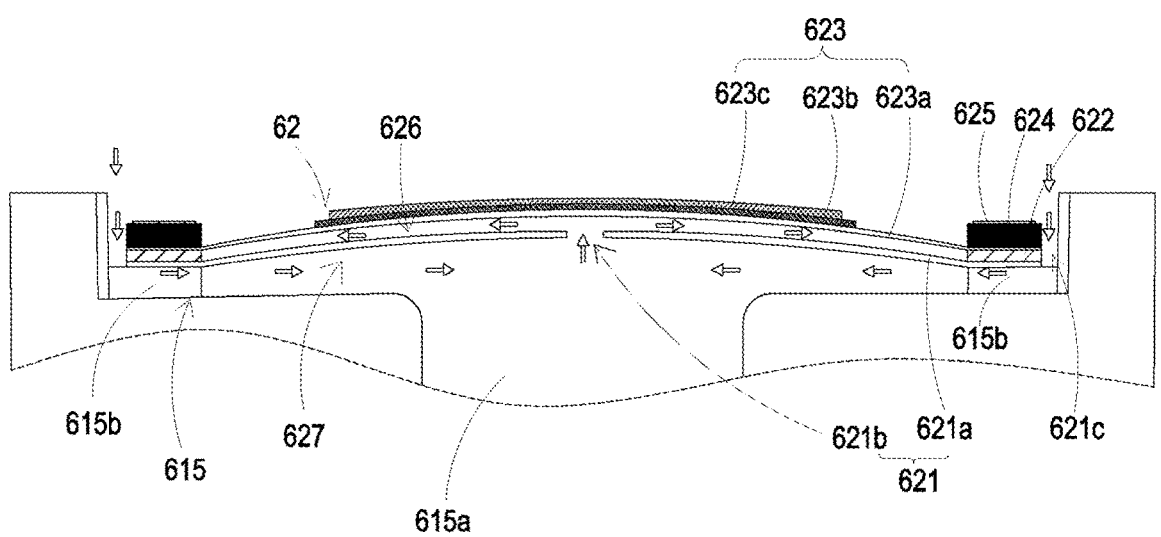
FIG. 18B and FIG. 18C illustrate schematic cross-sectional views showing the micro flow-guiding pump shown in FIG. 18A at different operation steps.
Figure 18C:
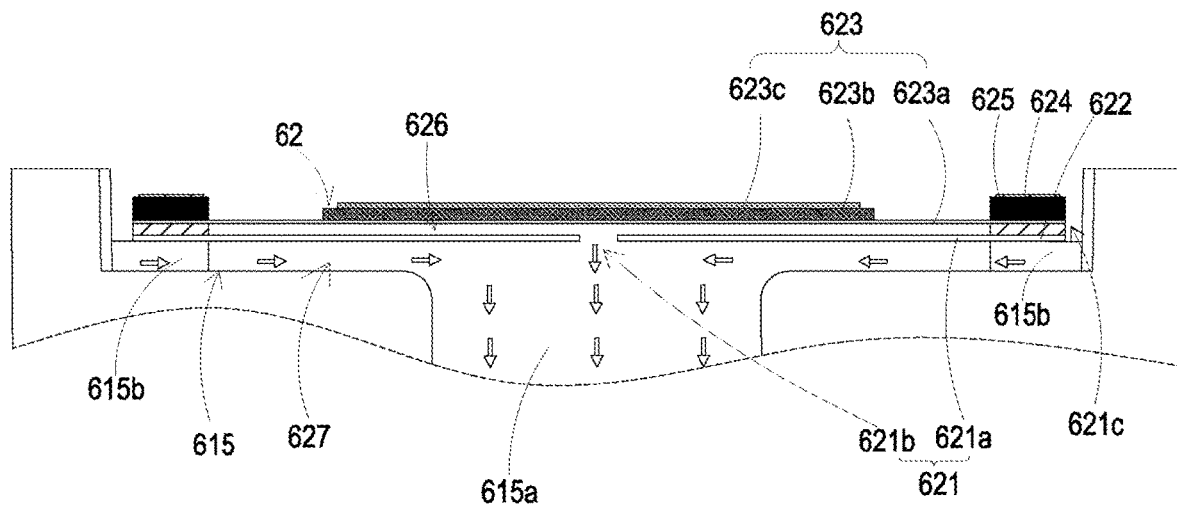

Please refer to FIG. 18B. When the piezoelectric plate 623c bends in a direction away from the bottom surface of the gas-guiding component loading region 615, the suspension sheet 621a of the nozzle plate 621 is driven by the piezoelectric plate 623c to bend in the direction away from the bottom surface of the gas-guiding component loading region 615 correspondingly. Hence, the volume of the gas flow chamber 627 expands dramatically, so that the internal pressure of the gas flow chamber 627 decreases and creates a negative pressure, thereby drawing the gas outside the micro flow-guiding pump 62 to flow into the micro flow-guiding pump 62 through the surrounding gap 621c, and enter into the resonance chamber 626 through the hollow hole 621b, thereby increasing the gas pressure of the resonance chamber 626 and thus generating a pressure gradient. Further, as shown in FIG. 18C, when the piezoelectric plate 623c drives the suspension sheet 621a of the nozzle plate 621 to move toward the bottom surface of the gas-guiding component loading region 615, the gas inside the resonance chamber 626 is pushed to flow out quickly through the hollow hole 621b so as to further push the gas inside the gas flow chamber 627, thereby the converged gas can be quickly and massively ejected and guided into the gas flowing hole 615a of the gas-guiding component loading region 615 in a state closing to an ideal gas state under the Benulli's law. Therefore, through repeating the steps as shown in FIG. 18B and FIG. 18C, the piezoelectric plate 623c can bend and vibrate reciprocatingly. Further, after the gas is discharged out of the resonance chamber 626, the internal pressure of the resonance chamber 626 is lower than the equilibrium pressure due to the inertia, as a result, the pressure difference guides the gas outside the resonance chamber 626 into the resonance chamber 626 again. Thus, through controlling the vibration frequency of the gas inside the resonance chamber 626 to be close to the vibration frequency of the piezoelectric plate 623c and generate the Helmholtz resonance effect, high-speed and large-volume gas transmission can be achieved.

Moreover, as shown in FIG. 19A, the gas enters into the gas detection module 6 from the gas inlet opening 661a of the outer cap 66, passes through the gas inlet through hole 614a and enters into the gas inlet groove 614 of the module body 61, and flows to the particulate sensor 65. As shown in FIG. 19B, the micro flow-guiding pump 62 continuously draws the gas into the gas inlet path so as to facilitate the gas outside the gas detection module 6 to be guided inside and to pass over the particulate sensor 65. At the same time, the light beam emitted by the laser component 64 passes through the light permissive window 614b and enters into the gas inlet groove 614. The particulate in the gas passing over the particulate sensor 65 in the gas inlet groove 614 are illuminated by the light beam. When the illuminated light beam encounters the particulate in the gas, the light beam scatters to generate light spots. The particulate sensor 65 receives and calculates the light spots generated by the scattering, such that the particulate sensor 65 obtains the related information regarding to particle size and the concentration of the particulate. And, the gas passing over the particulate sensor 65 is continuously guided into the gas flowing hole 615a of the gas-guiding component loading region 615 by the driving of the micro flow-guiding pump 62 and enters into the first region 616b of the gas outlet groove 616. Last, as shown in FIG. 19C, after the gas enters into the first region 616b of the gas outlet groove 616, since the micro flow-guiding pump 62 continuously delivers the gas into the first region 616b, the gas in the first region 616b is pushed toward the second region 616c, and the gas is eventually discharged out of the gas detection module 6 through the gas outlet through hole 616a and the gas outlet opening 661b.

Figure 20:
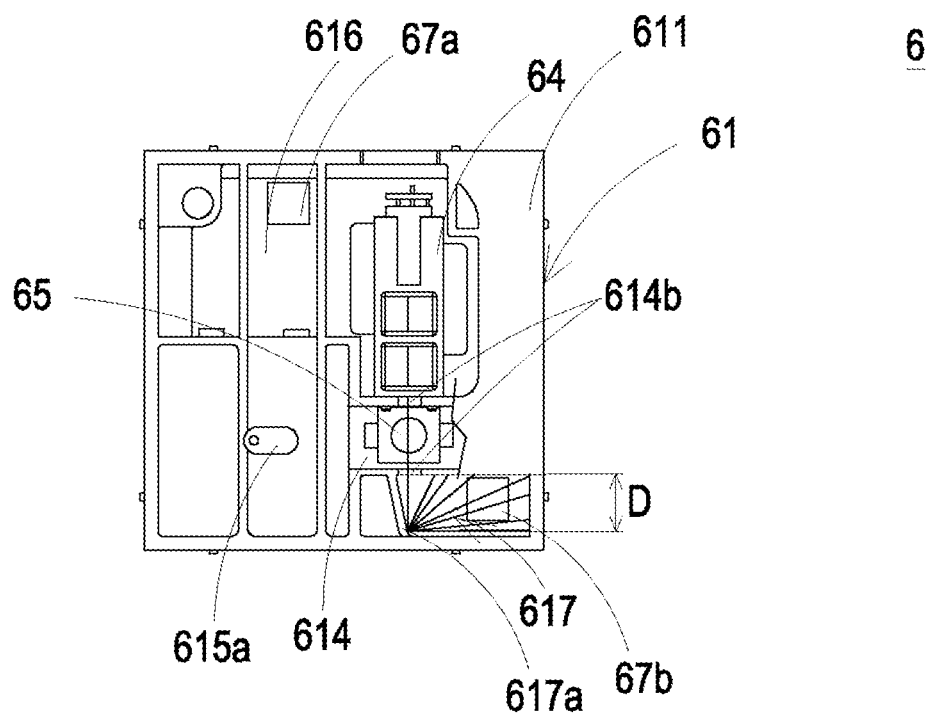
FIG. 20 illustrates a schematic cross-sectional view showing the laser beams emitted by the laser component of the gas detection module according to an exemplary embodiment of the present disclosure.

Furthermore, please refer to FIG. 20. The module body 61 may further include a light trap region 617. The light trap region 617 is formed by hollowing out the module body 61 from the first surface 611 toward the second surface 612, and the light trap region 617 corresponds to the laser configuration region 613. Moreover, the light trap region 617 passes through the light permissive window 614b, such that the light beam emitted by the laser component 64 can be projected into the light trap region 617. The light trap region 617 has a light trap structure 617a with an oblique cone surface, and the light trap structure 617a is corresponding to the path of the light beam emitted by the laser component 64. Moreover, the light trap structure 617a allows the light beam emitted by the laser component 64 to be reflected to the light trap region 617 by the oblique cone surface of the light trap structure 617a, thereby preventing the light beam from being reflected to the particulate sensor 65. Moreover, a light trap distance D is maintained between the light permissive window 614b and the position where the light trap structure 617a receives the light beam, thereby preventing stray light beams from being directly reflected to the particulate sensor 65 after the light beam projecting on the light trap structure 617a is reflected, and thus causing the distortion of detection accuracy.

Please refer to FIG. 13C and FIG. 20. The gas detection module 6 according to one or some embodiments of the present disclosure is not only capable of detecting the particles in the gas, but also capable of detecting the characteristics of the gas guided into the gas detection module 6, for example, the gas may be formaldehyde, ammonia, carbon monoxide, carbon dioxide, oxygen, ozone, and so on. Therefore, in one or some embodiments of the present disclosure, the structure of the gas detection module 6 further includes a first volatile organic compound sensor 67a. The first volatile organic compound sensor 67a is disposed on and electrically connected to the module driving board 63, and is received in the gas outlet groove 616 for detecting the gas guided out of the gas outlet path, so that the first volatile organic compound sensor 67a can be provided for detecting the concentration or the characteristics of the volatile organic compound contained in the gas guided out of the gas outlet path. Alternatively, in one or some embodiments of the present disclosure, the structure of the gas detection module 6 further includes a second volatile organic compound sensor 67b. The second volatile organic compound sensor 67b is disposed on and electrically connected to the module driving board 63. The second volatile organic compound sensor 67b is received in the light trap region 617 for detecting the concentration or the characteristics of the volatile organic compound contained in the gas passing through the gas inlet path of the gas inlet groove 614 and guided into the light trap region 617 through the light permissive window 614b.

Please refer to FIG. 1 and FIG. 2. The smart cloth may further include a gas detection module 6 packaged with and electrically connected to the control main board 2a of the control body 2 so as to detect the gas outside the cloth body 1 to generate gas data information and transmits to the microprocessor 2b, and transmits the gas data information to the external device 7 through the communication device 2d through the microprocessor 2b. Therefore, the smart cloth can alert or notify the person who is exposed to a place having the hazardous gas, so that the person can leave the place or take precautions for the hazardous gas, so as to prevented from having adverse impact in health or result in damages due to the exposure of hazardous gases.

As discussed above, the smart cloth of one or some embodiments of the present disclosure detects the temperature information of the wearer through the temperature sensing components and outputs the temperature information of the wearer to the microprocessor of the control body, so that the microprocessor controls the actuation pumps of the actuation air-permeable components to perform the gas-guiding operation so as to adjust the apparent temperature of the wearer to provide the wearing comfortableness. Moreover, the bio-sensing module, the blood glucose sensing module, and the blood pressure measurement module of the health-monitoring device detect are able to provide the detection data information anytime and in real-time so as to provide the health-related information to the wearer. Furthermore, the gas detection module can detect the gas to obtain the gas data information. Therefore, the smart cloth of this invention can alert or notify the person who is exposed to the hazardous gas so as to allow the person to leave the place or take precautions for the hazardous gas. Hence, the person can be prevented from having adverse impact in health or result in damages due to the exposure of hazardous gases. Accordingly, the smart cloth can have benefits of adjusting the apparent temperature of the wearer to provide the wearing comfortableness, detecting the health record anytime, and monitoring the air quality of ambient air.

The foregoing outlines features of several embodiments so that those skilled in the art may better understand the aspects of the present disclosure. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions, and alterations herein without departing from the spirit and scope of the present disclosure.

What is claimed is:

1. A smart cloth, comprising:
a cloth body comprising a pair of sleeves;
a control body comprising a microprocessor and a driving battery, wherein the microprocessor is connected to the driving battery, and wherein the microprocessor is capable of generating a first driving signal and a second driving signal, receiving temperature information and a plurality of detection data information, and outputting the first driving signal, the second driving signal, and the plurality of detection data information;
a plurality of actuation air-permeable components woven with and positioned on the cloth body, wherein the actuation air-permeable components comprise a plurality of actuation pumps, and the actuation pumps are series-connected to the microprocessor of the control body through conductors to receive the first driving signal of the microprocessor to perform a gas-guiding operation;
a plurality of temperature sensing components woven with and positioned on the cloth body, wherein the temperature sensing components comprise a plurality of temperature sensors, and the temperature sensors are series-connected to the microprocessor of the control body through conductors, and wherein the temperature sensors are capable of attaching to skin of a wearer to detect and generate the temperature information and output the temperature information to the microprocessor; and
a health-monitoring device woven with and positioned on the cloth body, wherein the health-monitoring device comprises a bio-sensing module, a blood glucose sensor, a blood pressure measurement module, and a gas bag, wherein the bio-sensing module, the blood glucose sensor, and the blood pressure measurement module are connected to the microprocessor of the control body through conductors, wherein the gas bag is woven and positioned on one of the pair of the sleeves of the cloth body, and the blood pressure measurement module is connected to the gas bag, wherein the bio-sensing module and the blood glucose sensor are capable of attaching to the skin of the wearer to generate the plurality of detection data information and provide the plurality of detection data information to the microprocessor for output, wherein the blood pressure measurement module receives the second driving signal of the microprocessor to perform the gas-guiding operation so as to inflate the gas bag which is capable of being worn on an arm portion of the wearer, such that the blood pressure measurement module is capable of detecting a blood pressure of the wearer to generate the plurality of detection data information and is capable of providing the microprocessor with the plurality of detection data information for output;

wherein the temperature information of the wearer is detected by the temperature sensing components and outputted to the microprocessor of the control body, so that the microprocessor controls the actuation pumps of the actuation air-permeable components to perform the gas-guiding operation so as to adjust an apparent temperature of the wearer to provide wearing comfortableness, and wherein the bio-sensing module, the blood glucose sensing module, and the blood pressure measurement module of the health-monitoring device detect the plurality of detection data information, and the bio-sensing module, the blood glucose sensing module, and the blood pressure measurement module of the health-monitoring device are capable of providing the plurality of detection data information anytime and in real-time so as to provide a health-related information to the wearer.

2. The smart cloth according to claim 1, wherein the bio-sensing module of the health-monitoring device is an integrated module of a photo-plethysmography sensor and an electrocardiography sensor, wherein the detection data information generated by the photo-plethysmography sensor is heart rate data information and pulse oxygen saturation information of the health-related information, and the detection data information generated by the electrocardiography sensor is electrocardiography data information of the health-related information.

3. The smart cloth according to claim 1, wherein the detection data information generated by the blood glucose sensor of the health-monitoring device is blood glucose graph data information of the health-related information.

4. The smart cloth according to claim 1, wherein the detection data information generated by the blood pressure measurement module of the health-monitoring device is blood pressure data information of the health-related information.

5. The smart cloth according to claim 1, wherein the actuation air-permeable components are formed by packaging the actuation pumps into a substrate through semiconductor manufacturing processes, so that the actuation pumps are series-connected to the microprocessor of the control body through the conductors.

6. The smart cloth according to claim 1, wherein the temperature sensing components are formed by packaging the temperature sensors into a substrate through semiconductor manufacturing processes, so that the temperature sensors are series-connected to the microprocessor of the control body through the conductors.

7. The smart cloth according to claim 5, wherein the substrate is a silicon substrate.

8. The smart cloth according to claim 6, wherein the substrate is a silicon substrate.

9. The smart cloth according to claim 1, wherein the control body comprises a control main board, wherein the microprocessor, the driving battery, and a communication device are packaged with and disposed on the control main board, and wherein the plurality of detection data information received by the microprocessor is transmitted to an external device through the communication device for storing, processing, or applying the plurality of detection data information.

10. The smart cloth according to claim 9, wherein the external device is one of a cloud system, a portable device, and a computer system.

11. The smart cloth according to claim 9, wherein the control main board comprises a plurality of contacts for connecting the actuation air-permeable components, the temperature sensing components, the bio-sensing module, the blood glucose sensor, and the blood pressure measurement sensor to the microprocessor through the conductors.

12. The smart cloth according to claim 9, further comprising a gas detection module, wherein the gas detection module is packaged with and electrically connected to the control main board of the control body, so that the gas detection module detects the gas outside the cloth body to generate gas data information and transmits the gas data information to the microprocessor, so that the microprocessor transmits the gas data information to the external device through the communication device for alerting and notifying.

13. The smart cloth according to claim 12, wherein the gas detection module comprises:
a module body having a first surface, a second surface, a laser configuration region, a gas inlet groove, a gas-guiding component loading region, and a gas outlet groove, wherein the second surface is opposite to the first surface, and the laser configuration region is hollowed out from the first surface to the second surface, wherein the gas inlet groove is recessed from the second surface and located adjacent to the laser configuration region, wherein the gas inlet groove has a gas inlet through hole and two lateral walls, wherein a light permissive window is opened on the lateral wall of the gas inlet groove and in communication with the laser configuration region, wherein the gas-guiding component loading region is recessed from the second surface and in communication with the gas inlet groove, wherein a gas flowing hole penetrates a bottom surface of the gas-guiding component loading region, and each of four corners of the gas-guiding component loading region has a positioning bump, wherein the gas outlet groove is recessed from a portion of the first surface corresponding to the bottom surface of the gas-guiding component loading region, and the gas outlet groove is hollowed out from the first surface to the second surface in a region where the first surface is not aligned with the gas-guiding component loading region, and wherein the gas outlet groove is in communication with the gas flowing hole, and the gas outlet groove has a gas outlet through hole;
a micro flow-guiding pump received in the gas-guiding component loading region;
a module driving board packaged with and electrically connected to the control board of the control body, and the micro flow-guiding pump is also packaged with and electrically connected to the module driving board to receive a third driving signal generated by the microprocessor to perform the gas-guiding operation, and the module driving board is attached to the second surface of the module body;
a laser component disposed on and electrically connected to the module driving board, wherein the laser component is received in the laser configuration region, and wherein a path of a light beam emitted by the laser component passes through the light permissive window and is orthogonal to the gas inlet groove;
a particulate sensor disposed on and electrically connected to the module driving board, wherein the particulate sensor is received in a portion of the gas inlet groove at a position where the path of the light beam emitted by the laser component is orthogonal to the gas inlet groove, so that the particulate sensor detects particulates passing through the gas inlet groove and illuminated by the light beam of the laser component;
a first volatile organic compound sensor disposed on and electrically connected to the module driving board, wherein the first volatile organic compound sensor is received in the gas outlet groove for detecting the gas so as to detect a concentration or characteristics of a volatile organic compound contained in the gas; and
an outer cap covering the first surface of the module body, wherein the outer cap has a side plate, wherein a portion of the side plate corresponding to the gas inlet through hole of the module body has a gas inlet opening, and another portion of the side plate corresponding to the gas outlet through hole of the module body has a gas outlet opening, and wherein the gas inlet opening is corresponding to the detection inlet of the module body, and the gas outlet opening is corresponding to the detection outlet of the module body;
wherein the outer cap is covered on the first surface of the module body, and the module driving board is covered on the second surface of the module body, so that the gas inlet groove defines a gas inlet path and the gas outlet groove defines a gas outlet path, wherein the micro flow-guiding pump receives the third driving signal generated by the microprocessor to perform the gas-guiding operation, thereby facilitating in guiding the gas out of the detection inlet of the module body into the gas inlet path defined by the gas inlet groove from the gas inlet opening, wherein the gas further passes through the particulate sensor, so that the particulate sensor detects a particle concentration of the gas, wherein the gas further passes through the first volatile organic compound sensor, so that the first volatile organic compound sensor detects the concentration or characteristics of the gas, wherein the gas is transmitted by the micro flow-guiding pump, the gas is discharged into the gas outlet path defined by the gas outlet groove from the gas flowing hole, and the gas is discharged out of the module body from the gas outlet through hole and the detection outlet of the module body so as to allow the gas detection module to detect the gas outside the cloth body to generate the gas data information and to transmit the gas data information to the microprocessor, and the microprocessor transmits the gas data information to the external device through the communication device.

14. The smart cloth according to claim 13, wherein the micro flow-guiding pump comprises:
a nozzle plate comprising a suspension sheet and a hollow hole, wherein the suspension sheet is capable of bending and vibrating, and the hollow hole is formed at a center portion of the suspension sheet;
a chamber frame stacked on the suspension sheet;
an actuation body stacked on the chamber frame so as to bend and vibrate reciprocatingly when the actuation body is applied with a voltage;
an insulation frame stacked on the actuation body; and
a conductive frame stacked on the insulation frame;
wherein the nozzle plate is fixedly disposed on and positioned with the positioning bumps in the gas-guiding component loading region, so that a surrounding gap is defined between the nozzle plate and an inner edge of the gas-guiding component loading region for the gas to flow therethrough, and a gas flow chamber is formed between a bottom of the nozzle plate and the bottom surface of the gas-guiding component loading region, wherein a resonance chamber is formed between the actuation body, the chamber frame, and the suspension sheet, and wherein the nozzle plate is capable of being driven to move correspondingly by driving the actuation body, so that the suspension sheet of the nozzle plate vibrates reciprocatingly, and thus the gas enters into the gas flow chamber through the surrounding gap and then is discharged out of the gas flow chamber, thereby achieving transmission of the gas.

15. The smart cloth according to claim 1, wherein the actuation pump is a microelectromechanical system pump and comprises:
a first substrate having a plurality of inlets;
a first oxide layer, formed and stacked on the first substrate, having a plurality of convergence troughs and a convergence chamber, wherein the convergence chamber is in communication with the inlets through the convergence troughs;
a second substrate combined with the first substrate, comprising:
a silicon wafer layer having an actuation portion, an outer peripheral portion, a plurality of connection portions, and a plurality of fluid channels, wherein the actuation portion is at a center portion of the silicon wafer layer, the outer peripheral portion surrounds a periphery of the actuation portion, and the connection portions are respectively connected between the actuation portion and the outer peripheral portion, and wherein the fluid channels surround the periphery of the actuation portion and are provided between the connection portions;
a second oxide layer formed on the silicon wafer layer, wherein the second oxide layer and the silicon wafer layer together define a vibration chamber; and
a silicon material layer formed on the second oxide layer, wherein the silicon material layer has a through hole, a vibration portion, and a fixed portion, and wherein the through hole is formed at a center portion of the silicon material layer, the vibration portion is located at a peripheral area of the through hole, and the fixed portion is located at a peripheral area of the silicon material layer; and
a piezoelectric component formed and stacked on the actuation portion of the silicon wafer layer, wherein the piezoelectric component comprises a lower electrode layer, a piezoelectric layer, an insulation layer, and an upper electrode layer, and wherein the piezoelectric layer is formed and stacked on the lower electrode layer, the insulation layer is disposed on a portion of a surface of the piezoelectric layer and a portion of a surface of the lower electrode layer, the upper electrode layer is formed and stacked on the insulation layer and a remaining portion of the surface of the piezoelectric layer where the insulation layer is not disposed, and the upper electrode layer is provided for being electrically connected to the piezoelectric layer.

16. The smart cloth according to claim 15, wherein a length of the actuation pump is between 300 μm and 800 μm, and a width of the actuation pump is between 300 μm and 800 μm.

17. The smart cloth according to claim 16, wherein the length of the actuation pump is between 500 μm and 700 μm, and the width of the actuation pump is between 500 μm and 700 μm.

18. The smart cloth according to claim 1, wherein the blood pressure measurement module comprises:
   a base having a valve loading area, an accommodation trough area, a gas inlet hole, and an insertion hole, wherein the valve loading area and the accommodation trough area are respectively disposed on different surfaces of the base, and the gas inlet hole and the insertion hole are in communication with the accommodation trough area, wherein the valve loading area comprises a first recessed receiving chamber and a second recessed receiving chamber, wherein a plurality of first through holes penetrates an inner wall of the first recessed receiving chamber and in communication with the accommodation trough area, and a first protruding structure extends from the first recessed receiving chamber at a center portion of the first recessed receiving chamber, wherein at least one second through hole penetrates an inner wall of the second recessed receiving chamber and in communication with the accommodation trough area, wherein an inner wall of the accommodation trough area is recessed to form a gas collection chamber and a sensor chamber, and the sensor chamber is adjacent to one side of the gas collection chamber and in communication with the gas collection chamber, gas inlet hole, and the insertion hole;
   a valve sheet disposed on the valve loading area, wherein the valve sheet comprises a valve hole corresponding to the first protruding structure;
   a top cover covering the valve loading area to seal the valve sheet and the insertion hole, wherein the top cover comprises an inlet channel, a discharge hole, and an assembling surface, wherein the inlet channel and the discharge hole are spaced apart from each other, wherein the assembling surface correspondingly covers the valve sheet, the assembling surface is recessed to form an inlet chamber in communication with the inlet channel, wherein the assembling surface is recessed to form a discharge chamber in corresponding to the discharge hole, wherein a second protruding structure extends from a center portion of the discharge chamber, and the discharge hole is defined through a center portion of the second protruding structure and in communication with the discharge chamber, so that the valve sheet and the second protruding structure normally abut against each other to generate a pre-force action and seal the discharge hole, wherein a communication groove is recessed between the inlet chamber and the discharge chamber, wherein the inlet channel is opposite to the assembling surface and in communication with the assembling surface, and wherein the inlet channel has a connection end and an extension end, the connection end is connected to the gas bag, the extension end extends from the connection end of the inlet channel to the insertion hole, and the extension end has a closing hole;
   a micro pump disposed in the accommodation trough area to cover the gas collection chamber;
   a driving circuit board covering the accommodation trough area, wherein the driving circuit board is connected to the microprocessor of the control body through the conductors so as to receive the second driving signal generated by the microprocessor of the control body and provide the micro pump with the second driving signal to control operation of the micro pump; and
   a pressure sensor disposed on and electrically connected to the driving circuit board, wherein the pressure sensor provides the detection data information to the microprocessor for output, wherein the pressure sensor is received in the sensor chamber of the accommodation trough area of the base, and the pressure sensor is inserted into the insertion hole of the base and received in the closing hole of the top cover, such that the pressure sensor is in communication with the inlet channel and is connected to the gas bag;
   wherein operation of the micro pump is controlled to perform gas transmission, so that gas outside the base is guided into the accommodation trough area through the gas inlet hole, and the gas is continuously guided to and converged in the gas collection chamber by the micro pump, so that the gas pushes the valve hole of the valve sheet so as to allow the valve sheet to be detached from the first protruding structure, thereby the gas passing through the valve hole is continuously guided into the inlet channel of the top cover and collected in the gas bag, whereby the gas inflates the gas bag to press the arm of the wearer, wherein the detection data information about blood pressure of the wearer is detected and calculated by the pressure sensor, and wherein the driving circuit board is connected to the microprocessor of the control body, so that the microprocessor receives the detection data information so as to output a notification of the detection data information about the blood pressure of the wearer.

19. The smart cloth according to claim 18, wherein the micro pump comprises:
   an inlet plate having at least one inlet hole, at least one convergence channel corresponding to the at least one inlet hole, and a convergence chamber, wherein the at least one inlet hole is configured to introduce the gas outside the micro pump to flow in the micro pump, and the at least one convergence channel is configured to guide the gas from the at least one inlet hole to be converged at the convergence chamber;
   a resonance sheet having a perforation corresponding to the convergence chamber, and a periphery of the perforation is a movable portion; and
   a piezoelectric actuator disposed in corresponding to the resonance sheet;
   wherein the inlet plate, the resonance sheet, and the piezoelectric actuator are sequentially stacked with each other, and wherein a chamber space is formed between the resonance sheet and the piezoelectric actuator, so that when the piezoelectric actuator is driven, the gas outside the micro pump is guided into the micro pump through the at least one inlet hole of the inlet plate, converged at the convergence chamber through the at least one convergence channel, and flowed through the perforation of the resonance sheet by a resonance effect between the piezoelectric actuator and the movable portion of the resonance sheet.

20. The smart cloth according to claim 1, wherein the microprocessor of the control body provides the second driving signal to the blood pressure measurement module to detect a blood pressure condition of the wearer, and wherein the blood pressure condition detected by the blood pressure measure module including generating a trend information of detection data in a period of time, and the period of time is one or several days, one or several weeks, one or several months, or one or several years.

\* \* \* \* \*